(12) United States Patent
Hou et al.

(10) Patent No.: US 12,098,479 B2
(45) Date of Patent: Sep. 24, 2024

(54) PROBIOTIC-ENCAPSULATING GUM ARABIC COMPOSITE FIBER/CAPSULE, PREPARATION METHOD AND APPLICATION THEREOF

(71) Applicant: Northeast Agricultural University, Harbin (CN)

(72) Inventors: Juncai Hou, Harbin (CN); Jiage Ma, Harbin (CN); Zhanmei Jiang, Harbin (CN); Cong Xu, Harbin (CN); Wan Wang, Harbin (CN)

(73) Assignee: Northeast Agricultural University, Harbin (CN)

( * ) Notice: Subject to any disclaimer, the term of this patent is extended or adjusted under 35 U.S.C. 154(b) by 0 days.

(21) Appl. No.: 18/150,519

(22) Filed: Jan. 5, 2023

(65) Prior Publication Data
US 2023/0193514 A1   Jun. 22, 2023

(30) Foreign Application Priority Data
Jan. 7, 2022 (CN) .......................... 202210013148.3

(51) Int. Cl.
| | | |
|---|---|---|
| *D01D 5/00* | (2006.01) | |
| *A61K 9/00* | (2006.01) | |
| *C12N 1/20* | (2006.01) | |
| *C12N 11/04* | (2006.01) | |
| *D01F 1/10* | (2006.01) | |

(52) U.S. Cl.
CPC ......... *D01D 5/0007* (2013.01); *A61K 9/0092* (2013.01); *C12N 1/20* (2013.01); *C12N 11/04* (2013.01); *D01F 1/10* (2013.01); *D01D 5/0076* (2013.01)

(58) Field of Classification Search
CPC .... D01D 5/0007; D01D 5/0076; D01D 5/003; A61K 9/0092; A61K 9/503; A61K 9/5036; C12N 1/20; C12N 11/04; C12R 2001/225; C12R 2001/25; D01F 1/10; Y02A 50/30
See application file for complete search history.

(56) References Cited

U.S. PATENT DOCUMENTS

2015/0209469 A1   7/2015   McKiernan et al.
2016/0032271 A1   2/2016   Kuhn et al.

FOREIGN PATENT DOCUMENTS

| CN | 103283975 A | 9/2013 |
|---|---|---|
| CN | 108589045 A | 9/2018 |
| CN | 112741328 A | 5/2021 |
| EP | 2646006 B1 | 2/2015 |

OTHER PUBLICATIONS

Ma et al. (Food Hydrocolloids. 111 (2021) 106381 pp. 1-7; available online: Oct. 2, 2020) (Year: 2020).*
Tsai et al. (Carbohydrate Polymers 115 (2015) 525-532) (Year: 2015).*
Ma et al. (Food Hydrocolloids. 111 (2021) 106381 pp. 1-7; available online: Oct. 2, 2020) (Year: 2020) (Year: 2020).*
Tsai et al. (Carbohydrate Polymers 115 (2015) 525-532) (Year: 2015) (Year: 2015).*
Amparo Lopez-Rubio et al., "Encapsulation of living bifidobacteria in ultrathin PVOH electrospun fibers", Biomacromolecules, 2009, vol. 10, No. 10, pp. 2823-2829.
Jiage Ma et al., "Electro-encapsulation of probiotics in gum Arabic-pullulan blend nanofibres using electrospinning technology", Food Hydrocolloids, pp. 1-24.
Tian Jiang et al., "Electrostatic spray drying microencapsulated Bifidobacterium lactis BL03", Food and Fermentation Industries, 2021, vol. 47, No. 7, pp. 27-33.
Cong Xu et al., "Advances in the Application of Electrospinning Technology in Food Industry", Science and Technology of Food Industry, 2021, vol. 42, No. 2, pp. 370-378.

* cited by examiner

*Primary Examiner* — Anna R Falkowitz

(57) ABSTRACT

A probiotic-encapsulating gum Arabic (GA) composite fiber/capsule, including: lactic acid bacteria and an electrospun fiber or electrosprayed capsule, where the lactic acid bacteria are encapsulated in the electrospun fiber or electrosprayed capsule by electro-hydro dynamics (EHD) technology. The electrospun fiber or electrosprayed capsule is prepared by compounding a polymer matrix with GA, and the polymer matrix is polyvinyl alcohol (PVOH), polyvinylpyrrolidone (PVP), whey protein concentrate (WPC) or maltodextrin (MD). A preparation method and an application of the composite fiber/capsule are also provided.

7 Claims, 23 Drawing Sheets

PROBIOTIC-ENCAPSULATING GUM ARABIC COMPOSITE FIBER/CAPSULE, PREPARATION METHOD AND APPLICATION THEREOF

CROSS-REFERENCE TO RELATED APPLICATIONS

This application claims the benefit of priority from Chinese Patent Application No. 202210013148.3, filed on Jan. 7, 2022. The content of the aforementioned application, including any intervening amendments thereto, is incorporated herein by reference in its entirety.

TECHNICAL FIELD

This application relates to probiotics, and more particularly to a probiotic-encapsulating gum Arabic composite fiber/capsule, a preparation method and application thereof.

BACKGROUND

Probiotics are defined as "live microorganisms" which confer a health benefit to the host when administered in adequate amounts. Health benefits of probiotics have attracted considerable attention, and the consumption of probiotic products is promoted. *Lactobacillus* has been widely employed as probiotics in the food industry due to abilities to regulate the host intestinal flora, inhibit pathogenic bacteria, and improve human health. To achieve these health benefits, there should be minimum $10^6$-$10^7$ CFU/g of viable probiotics at the time of consumption. However, *Lactobacillus* is sensitive to extreme environmental conditions, and have poor processing and storage stability. Moreover, they also have low bioavailability when exposed to gastrointestinal conditions. When processed, and stored in the host's gastrointestinal tract, *Lactobacillus* will inevitably be subjected to various stresses from the external environment, thereby affecting stability and bioavailability and greatly limiting the probiotic effect and application in the food industry. The existing probiotics encapsulation methods mostly involve high or low temperature processing and organic solvents, which will easily cause viability loss and safety risks. In view of this, extensive attempts have been made to incorporate feasible technologies, such as electro-hydrodynamic microencapsulation technology, to synergistically enhance the prebiotic efficiency, protect probiotics against multiple environmental stresses while ensuring the probiotic efficacy, and improve the stability and function of probiotics.

SUMMARY

In view of the deficiencies in the prior art, this application provides a probiotic-encapsulating gum Arabic (GA) composite fiber/capsule, a preparation method and application thereof. Lactic acid bacteria are encapsulated in the electrospun fibers or electrosprayed capsules formed by compounding a matrix with the prebiotic GA to improve the processing and storage stability and survival rate of lactic acid bacteria, where the matrix is a synthetic biopolymer, such as polyvinyl alcohol (PVOH) and polyvinylpyrrolidone (PVP), or a food-grade polymer, such as whey protein concentrate (WPC) and maltodextrin (MD).

Technical solutions of this application are described as follows.

In a first aspect, this application provides a probiotic-encapsulating GA composite fiber/capsule, including:
lactic acid bacteria; and
an electrospun fiber or an electrosprayed capsule;
wherein the lactic acid bacteria are encapsulated in the electrospun fiber or electrosprayed capsule; the electrospun fiber or electrosprayed capsule is prepared by compounding a biopolymer matrix with GA; and the biopolymer matrix is selected from the group consisting of polyvinyl alcohol, polyvinylpyrrolidone and whey protein;
when the biopolymer matrix is polyvinyl alcohol or polyvinylpyrrolidone, the probiotic-encapsulating GA composite fiber/capsule is prepared through steps of:
(a1) preparing a suspension of the lactic acid bacteria; dissolving GA powder in water to obtain a GA solution; dissolving the polyvinyl alcohol or polyvinylpyrrolidone in water to obtain a biopolymer solution; and mixing the biopolymer solution with the GA solution uniformly to obtain a first mixed solution;
(a2) adding the suspension of the lactic acid bacteria to the first mixed solution followed by uniform stirring to obtain a second mixed solution; and
(a3) adding an additive to the second mixed solution followed by electrospinning to obtain the probiotic-encapsulating GA composite fiber or electrospraying to obtain the probiotic-encapsulating GA composite capsule;
when the biopolymer matrix is the whey protein or maltodextrin (MD), the probiotic-encapsulating GA composite fiber/capsule is prepared through steps of:
(b1) preparing a suspension of the lactic acid bacteria; dissolving GA powder in water to obtain a GA solution; adding the whey protein to the GA solution followed by mixing and stirring to obtain a first mixed solution;
(b2) adding the suspension of the lactic acid bacteria to the first mixed solution followed by uniform stirring to obtain a second mixed solution; and
(b3) adding an additive to the second mixed solution followed by electrospinning to obtain the probiotic-encapsulating GA composite fiber or electrospraying to obtain the probiotic-encapsulating GA composite capsule; and
in step (a3), the additive is tween 80, and is 5% of a weight of the polyvinyl alcohol or polyvinylpyrrolidone in the second mixed solution; and in step (b3), the additive is tween 80, and is 5% of a weight of the whey protein in the second mixed solution.

In an embodiment, the lactic acid bacteria are *Lactobacillus plantarum* KLDS 1.0328.

In an embodiment, a diameter of the electrospun fiber is 150~170 nm, and a diameter of the electrosprayed capsule is 0.8~1.2 μm.

In an embodiment, in the steps (a1) and (b1), the suspension of the lactic acid bacteria is prepared through the following steps:
inoculating the lactic acid bacteria into a deMan, Rosa and Sharpe (MRS) liquid medium at an inoculum amount of 2%, followed by anaerobic culture at 35~39° C. for 20~24 h and centrifugation at 4° C. and 5000×g for 10 min to collect cells; and
washing the cells with a sterile phosphate-buffered saline (PBS) followed by resuspending with the PBS to a cell concentration of $10^9$~$10^{10}$ CFU/mL to produce the suspension of the lactic acid bacteria.

In an embodiment, in the step (a1), a weight/volume percent concentration of the GA solution is 20%; a weight/ volume percent concentration of the biopolymer solution is 10%; and a weight ratio of the biopolymer solution to the GA solution is 8:2; and in the step (b1), a weight/volume percent concentration of the GA solution is 4%, and a weight/volume percent concentration of the whey protein in the first mixed solution is 20%.

In an embodiment, in the step (a2), a concentration of the lactic acid bacteria in the second mixed solution is $10^9 \sim 10^{10}$ CFU/mL; and in the step (b2), a concentration of the lactic acid bacteria in the second mixed solution is $10^9 \sim 10^{10}$ CFU/mL.

In an embodiment, in the steps (a3) and (b3), the electrospinning or the electrospraying is carried out at a voltage of 16~21 kV, a flow rate of 0.3~1.0 mL/h, and a working distance of 10~16 cm.

This application further provides an application of the probiotic-encapsulating GA composite fiber/capsule in the preparation of a food, drug and/or a health-care product.

Compared to the prior art, this application has the following beneficial effects.

The electrosprayed capsules obtained herein are powder having readily-processed physical appearance, and the electrospun fibers are continuous fiber mats. Generally, the electrosprayed capsules are suitable as food additives, and the electrospun fiber mats can be used mainly in the packaging of bioactive food.

The prebiotic GA-modified electrospun nanofibers and electrosprayed capsules have great potential for application in functional foods and are conducive to the development of stable probiotic delivery systems.

Lactic acid bacteria are successfully encapsulated in the electrospun fibers or electrosprayed capsules by the electrohydro dynamics (EHD) technology, where the electrospun fibers or electrosprayed capsules is prepared by compounding PVOH, PVP, WPC or MD (as the matrix) with GA. The encapsulation systems constructed by different polymer solutions vary in morphology, and the bacteria can be directionally encapsulated along the nanofibers or randomly distributed in the capsules. There may be more intramolecular and intermolecular hydrogen-bond interactions between the biopolymer and the bacteria, such that the composite fiber/capsule has the potential to be applied in heat-treated foods. PVOH/GA fibers have the highest encapsulation rate, and lead to the highest survival rate for the bacteria in the simulated gastrointestinal tract, followed by WPC/GA and PVP/GA systems. The addition of GA can effectively improve the ability of electrosprayed capsules to resist stresses from the simulated gastrointestinal tract. PVOH/GA fibers and WPC/GA capsules have strong resistance to osmotic stress, and high-temperature and high-humidity stresses, and have lower viability loss after 28-d storage at 25° C. and 4° C. By contrast, the stability of bacteria in the MD/GA is relatively poor. After the encapsulation matrix is rehydrated, the bacteria still retain the original metabolic acid-producing and bacterial inhibition abilities. This application lays a theoretical foundation for the preparation of the probiotic encapsulation system by EHD technology and the improvement of stress resistance of lactic acid bacteria.

DETAILED DESCRIPTION OF EMBODIMENTS

Figure 1:
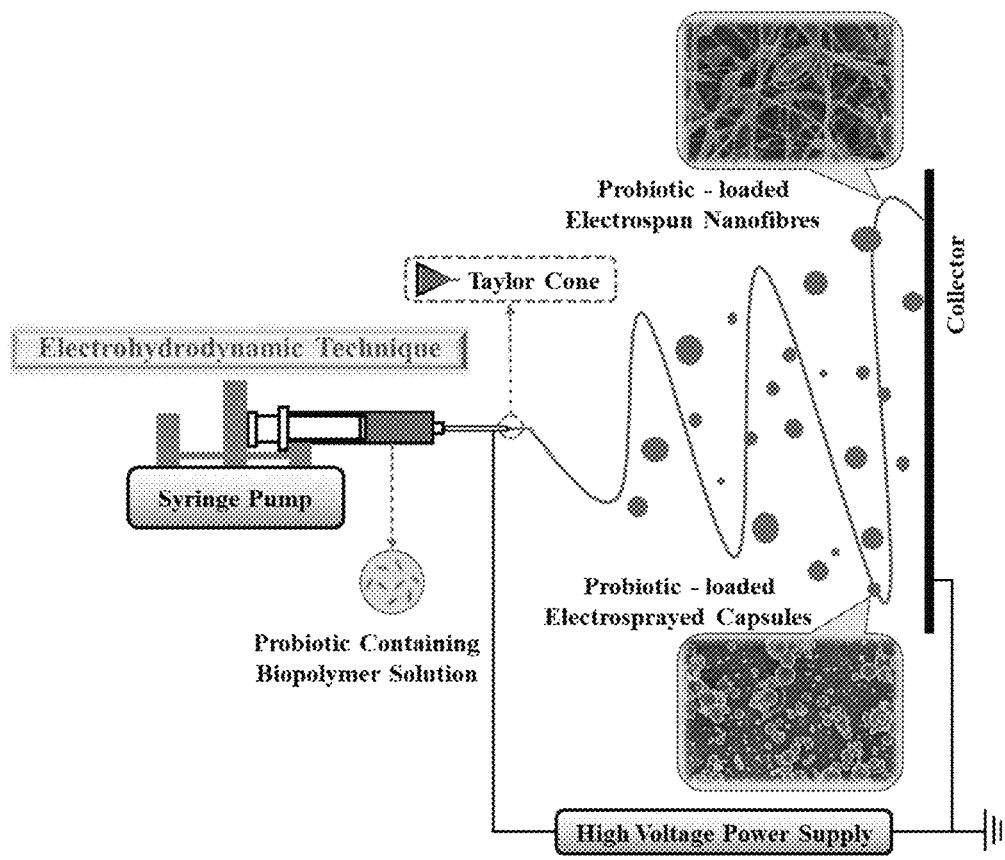
FIG. 1 schematically shows an electro-hydro dynamics (EHD) process.

The present disclosure will be described in detail below with reference to the embodiments. It should be noted that these embodiments are merely illustrative to facilitate the understanding of the technical solutions of the disclosure, and are not intended to limit the disclosure.

EXAMPLE

1. Experimental Materials

*Lactobacillus plantarum* KLDS 1.0328 used herein was isolated from traditional fermented pickles made in Heilongjiang Province, China, and stored in the Key Laboratory of Dairy Science, Ministry of Education, Northeast Agricultural University. *Staphylococcus aureus* CMCC 26003, *Salmonella Typhimurium* ATCC 14028 and *Escherichia coli* ATCC 25922 were reserved in the Key Laboratory of Dairy Science, Ministry of Education. The rest of the materials were existing technical materials and equipment, which could be purchased from the market and would not be repeated here.

2. Experimental Design and Method 2.1 Activation and Culture of Strains

The *Lactobacillus* test strain stored in a glycerol cryopreservation tube at −80° C. was removed, inoculated at an inoculum amount of 2% (v/v) in MRS medium and cultured at 37° C. for 24 h, and activated three times continuously to restore the viability of the strain. A small amount of bacterial solution was picked up by an inoculation loop, then streaked on a MRS agar plate by the three-sector streak method and cultured at 37° C. After 24 h, single colonies were selected, followed by performing Gram staining and microscopical examination to identify pure culture, and passaged in MRS medium twice more times until *Lactobacillus* strain was revived.

2.2 Preparation of *Lactobacillus* Suspension

*L. plantarum* KLDS 1.0328 was added to MRS medium at an inoculum amount of 2% (v/v) and incubated anaerobically at 37° C. for 20 h. Then the fermented liquid was centrifuged at 5000×g and 4° C. for 10 min, washed 3 times with sterile PBS buffer (pH 7.2), and then the *L. plantarum* KLDS 1.0328 was resuspended in sterile PBS buffer, and the concentration of the cell suspension was adjusted to obtain about $10^9$-$10^{10}$ CFU/mL, and placed at 4° C. for reserve.

2.3 Preparation of Electrospinning and Electrospraying Solution

A certain mass of the GA powder was weighed, dissolved in deionized water, and stirred at 600 rpm using MIXdrive 6 magnetic stirrer for 4 h at room temperature to obtain GA solution with a concentration of 4% (w/v) and 20% (w/v), respectively. After that, GA solution with different concentrations was left for overnight at 4° C., and the GA solution was centrifuged at 3000×g and room temperature for 5 min to remove insoluble matter.

A certain mass of polyvinyl alcohol (PVOH) and polyvinylpyrrolidone (PVP) were weighed, dissolved in deionized water, and stirred for 30 min in a water bath at 60° C., and then stirred at 95° C. for 2 h to obtain uniform 10% (w/v) PVOH and 10% (w/v) PVP solution, respectively. PVOH (10% w/v) or PVP solution (10% w/v) was mixed with 20% (w/v) GA solution in a ratio of 8:2 (w/w) followed by magnetically stirring at 600 rpm, 25° C. for 2 h to obtain PVOH/GA mixed solution or PVP/GA mixed solution. 4% (w/v) GA solution was used as the base solvent, whey protein concentrate (WPC) or maltodextrin (MD) was added to the GA solution and stirred magnetically at 600 rpm, 25° C. for 2 h to obtain WPC/GA solution or MD/GA solution with concentration of 20% (w/v), respectively.

*L. plantarum* KLDS 1.0328 was resuspended in the above electrospinning or electrospraying biopolymer solution, and continuously stirred on the magnetic stirrer at 600 rpm for 1 h to obtain *lactobacillus* suspension of about $10^9$-$10^{10}$ CFU/mL. Finally, Tween 80 was added to all solutions at the concentration of 5% (w/w) relative to the biopolymer in solution to assist the EHD process.

2.4 Determination of Properties of Electrospinning and Electrospraying Solution (1) pH: PHS-3C precision pH meter was used to determine pH of different kinds of biopolymer solutions in the presence or in the absence of *L. plantarum* KLDS 1.0328 at (25±0.1° C.)

(2) Conductivity: the conductivity of different kinds of biopolymer solutions in the presence or in the absence of *L. plantarum* KLDS 1.0328 was determined at (25±0.1° C.) by using a Delta 326 conductivity meter.

(3) Viscosity: DV3TLVTJ0 digital viscometer was used to measure the viscosity of different kinds of biopolymer solutions in the presence or in the absence of *L. plantarum* KLDS 1.0328. The LV-04 (64) rotor was used to stir the solutions at 200 rpm, and the viscosity was measured (25±0.1° C.) in the water bath.

2.5 Construction of Carrier of *L. plantarum* KLDS 1.0328 Based on EHD Technology The electrospinning solution or electrospraying solution prepared in the step (2.3) was added to a 10 mL sterile syringe and fixed on a propulsion pump. The electrospinning or electrospraying process was carried out in horizontal mode, as shown in FIG. 1. The two ends of the high-voltage DC power supply were fixed on the front end of the needle and the grounded metal receiving plate, and the needle used a 18G stainless steel needle. The biopolymer solution can form a relatively stable Taylor cone at the stainless steel needle, and the preliminary process parameters (voltage, flow rate, and distance between the syringe tip and the collector) during the EHD process were shown in Table 1. The temperature of the test environment was (25±0.1° C.), and the relative humidity was 40~50%. The electrospun fibers or electrosprayed capsules were collected on the grounded receiving metal plate covered with aluminum foil (15×15 cm). The final products obtained are PVOH/GA electrospun fibers, PVP/GA electrospun fibers, WPC/GA electrosprayed capsules, and MD/GA electrosprayed capsules, which were all encapsulated with probiotics.

TABLE 1

Process parameters of the EHD process

| Matrix | Voltage (kV) | Flow rate(mL/h) | Distance (cm) |
|---|---|---|---|
| PVOH | 21.0 | 0.6 | 16.0 |
| PVP | 17.0 | 1.0 | 12.0 |

TABLE 1-continued

Process parameters of the EHD process

| Matrix | Voltage (kV) | Flow rate(mL/h) | Distance (cm) |
|---|---|---|---|
| WPC | 17.0 | 0.4 | 12.0 |
| MD | 16.0 | 0.3 | 10.0 |

2.6 Characterization of the Electrospun Fibers/Electrosprayed Capsules (1) Scanning electron microscopy (SEM) analysis The prepared electrospun fibers or electrosprayed capsules were pasted on the conductive glue of the sample stage, and then the gold coating was plated under vacuum for 120 s by the ion sputtering coating instrument, and the current intensity was 20 mA. The morphology of the samples was observed using SEM. Fifty fibers or particles were randomly selected from different SEM images and measured with Image J software (Maryland, USA) to obtain the average diameter of the samples.

(2) Inverted fluorescence microscope analysis

L. plantarum KLDS 1.0328 was stained. The fluorescent dye rhodamine 123 was dissolved in dimethyl sulfoxide to obtain 1 mg/mL rhodamine 123 fluorescent stain. The fluorescent stain was added to the cell PBS suspension with an amount of 3 μg/mL, mixed well, and incubated at 37° C. for 20 min. The fluorescently labeled cell PBS suspension was centrifuged at 5000×g for 10 min, the cell pellet was collected and resuspended in different kinds of polymer solutions. After the slides were attached to aluminum foil, the process of electrokinetic encapsulation of cells was proceeded.

(3) Attenuated total reflection-Fourier transform infrared spectroscopy (ATR FTIRs) analysis The prepared electrospun fibers or electrosprayed capsules were placed on the test bench, and the infrared spectrum was recorded by attenuated total reflection Fourier transform infrared spectroscopy (ATR-FTIR) analysis with the wavelength range of 4000~525 $cm^{-1}$, 4 $cm^{-1}$ resolution, and 32 scanning times.

(4) Thermogravimetric analysis (TGA)

The electrospun fibers and electrosprayed capsules were ground and crushed. About 5 mg of the above samples were weighed and placed in the thermogravimetric analyzer, and heated to 600° C. from room temperature at the heating rate of 10° C./min. The electrospun fiber and electrosprayed capsule samples were thermally analyzed. A constant nitrogen atmosphere was added at 50 mL/min throughout the process.

2.7 Study on Stress Resistance of the Electrospun Fibers/Electrosprayed Capsules Encapsulated with L. plantarum KLDS 1.0328

(1) Viability determination of L. plantarum KLDS 1.0328 cells encapsulated in the electrospun fibers/electrosprayed capsules L. plantarum KLDS 1.0328 cells were thoroughly mixed with biopolymer solution by gradient dilution and pour plate method, and cell viability was determined before the electrospinning or electrospraying process. After the electrospun fibers or electrosprayed capsules were obtained, the samples encapsulated with L. plantarum KLDS 1.0328 were placed in sterile PBS buffer (pH 7.2) and shaken at 37° C., 100 rpm in a shaking incubator for 30 min to allow sufficient release of cells from the encapsulating material to estimate the viable cell count. Then, after the samples were placed in 0.85% (w/v) sterile normal saline, serial dilution was followed to reach the suitable dilution, and the pour plate method was carried on. After incubation for 48 h at 37° C., the viability of L. plantarum KLDS 1.0328 was expressed as viable cell count (lg CFU/g). The encapsulation rate was calculated by the following formula.

$$\text{Encapsulation rate} = (N_{post}/N_{pre}) \times 100\%$$

In the formula, $N_{pre}$ and $N_{post}$ represent the viable cell count (lg CFU/g) in electrospinning/electrospraying solution before and after the EHD process, respectively.

(2) Tolerance of L. plantarum KLDS 1.0328 encapsulated in the electrospun fibers/electrosprayed capsules to in vitro simulated gastrointestinal environment Sodium chloride (6.23 g/L), potassium chloride (2.29 g/L), calcium chloride (0.229 g/L), and sodium bicarbonate (1.2 g/L) were dissolved in sterile distilled water; pH was adjusted to 2.3 with 0.1 mol/L HCl; pepsin with the final concentration of 3 g/L was added; and filtration sterilization was performed with an aqueous membrane of 0.45 μm to prepare Simulated Gastric Fluid (SGF). Appropriate amount of 0.239 g/L potassium chloride, 1.28 g/L sodium chloride and 6.4 g/L calcium bicarbonate were dissolved in sterile distilled water; pH was adjusted to 8.0 with 0.1 mol/L NaOH; bile salt with the final concentration of 4.5 g/L was added; trypsin with the final concentration of 1 g/L was added; and filtration sterilization was performed with an aqueous membrane of 0.45 μm to prepare Simulated Intestinal Fluid (SIF). 500 mg of electrospun fibers or electrosprayed capsules were placed in 4.5 mL sterile SGF and exposed in the shaking incubator at 37° C., 100 rpm for 120 min. Meanwhile, 500 μL of free L. plantarum KLDS 1.0328 cell suspension under the same conditions was used as a control group. The samples were then recollected by centrifugation at 5000×g for 10 min, resuspended in 4.5 mL of sterile SIF, and exposed for 120 min in the shaking incubator at 37° C., 100 rpm. Bacterial colonies per gram were measured by MRS agar plate colony counting method. (3) Study on the tolerance of L. plantarum KLDS 1.0328 encapsulated in the electrospun fibers/electrosprayed capsules to osmotic stress and humidity and heat stress conditions.

To evaluate the effect of the osmotic stress on the tolerance of the encapsulated L. plantarum KLDS 1.0328, 2%, 4%, and 6% NaCl were added to sterile PBS buffer, respectively, and about 500 mg of electrospun fiber or electrosprayed capsules were added to 4.5 mL of the above solution, respectively. Free L. plantarum KLDS 1.0328 cell suspension under the same conditions was used as a control group. Before exposure to osmotic stress and after 3 h exposure to osmotic stress, bacterial colonies per gram were measured by MRS agar plate colony counting method.

To evaluate the effect of the humidity and heat stress conditions on the tolerance of the encapsulated L. plantarum KLDS 1.0328, free L. plantarum KLDS 1.0328 cell suspension in the control group and electrospun fibers or electrosprayed capsules encapsulated with L. plantarum KLDS 1.0328 cells were added to sterile tubes with 4.5 mL of sterile PBS buffer, and then incubated in water baths at 50° C., 60° C., and 70° C., respectively. Before exposure to humidity and heat stress conditions and after 30 min exposure to humidity and heat stress conditions, bacterial colonies per gram were measured by MRS agar plate colony counting method.

2.8 Storage Stability Study of *L. plantarum* KLDS 1.0328 Encapsulated in the Electrospun Fibers/Electrosprayed Capsules The electrospun fibers or electrosprayed capsules encapsulated with *L. plantarum* KLDS 1.0328 were placed in a sterile glass tube with lid, then placed in a sealed bag, and stored at 4° C. and 25° C. for 28 d, respectively. Bacterial colonies were counted by the gradient dilution and the pour plate method at 0 d, 7 d, 14 d, 21 d and 28 d, respectively.

2.9 Study on the Biological Characteristics of *L. plantarum* KLDS 1.0328 Encapsulated in the Electrospun Fibers/Electrosprayed Capsules (1) Effect of the electrospinning and electrospraying process on metabolism of *L. plantarum* KLDS 1.0328

The electrospun fibers or electrosprayed capsules encapsulated with *L. plantarum* KLDS 1.0328 were placed in sterile PBS buffer (pH 7.2) and shaken at 37° C., 100 rpm in the shaking incubator for 30 min. 1 mL of free *L. plantarum* KLDS 1.0328 cell suspension or rehydrated electrospun fibers or rehydrated electrosprayed capsules were added to 49 mL of sterile MRS liquid medium and incubated anaerobically at 37° C. for 24 h. The fermented liquid was taken out every 4 h, and pH of the culture medium was measured by the PHS-3C precision pH meter.

(2) Effect of the electrospinning and electrospraying process on the bacteriostatic activity of *L. plantarum* KLDS 1.0328

The electrospun fibers or electrosprayed capsules encapsulated with *L. plantarum* KLDS 1.0328 were placed in sterile PBS buffer (pH 7.2) and shaken at 37° C., 100 rpm in the shaking incubator for 30 min. 0.5 mL of free *L. plantarum* KLDS 1.0328 cell suspension or rehydrated electrospun fibers or rehydrated electrosprayed capsules were inoculated in 4.5 mL of sterile MRS liquid medium and incubated anaerobically at 37° C. for 24 h. After incubation, the effect of *L. plantarum* KLDS 1.0328 on the bacteriostatic activity of the indicator bacteria such as *S. aureus* CMCC 26003, *S. Typhimurium* ATCC 14028 and *E. coli* ATCC 25922 was evaluated by the Oxford Cup agar diffusion method.

3. Results and Analysis 3.1 The effect of compositions on the properties of the electrospinning and electrospraying solution was determined, and the pH, conductivity and viscosity of the electrospinning and electrospraying solutions with different compositions were shown in Table 2.

TABLE 2

Properties of different electrospinning/electrospraying solutions

| Composition | pH | Conductivity (mS/cm) | Viscosity (cp) |
|---|---|---|---|
| PVOH | $7.96 \pm 0.02^{a}$ | $6.32 \pm 0.04^{f}$ | $278.1 \pm 6.2^{e}$ |
| PVOH/GA | $6.05 \pm 0.01^{e}$ | $8.19 \pm 0.11^{e}$ | $392.6 \pm 6.9^{b}$ |
| PVOH/GA/*L. plantarum* KLDS 1.0328 | $6.01 \pm 0.01^{e}$ | $8.89 \pm 0.03^{d}$ | $544.0 \pm 4.6^{a}$ |
| PVP | $5.36 \pm 0.03^{f}$ | $0.37 \pm 0.00^{k}$ | $190.0 \pm 4.5^{i}$ |
| PVP/GA | $4.64 \pm 0.01^{hi}$ | $3.00 \pm 0.04^{i}$ | $237.0 \pm 0.0^{g}$ |
| PVP/GA/*L. plantarum* KLDS 1.0328 | $4.61 \pm 0.01^{i}$ | $3.96 \pm 0.02^{h}$ | $264.2 \pm 3.3^{f}$ |
| WPC | $6.50 \pm 0.00^{b}$ | $24.17 \pm 0.40^{c}$ | $6.0 \pm 0.0^{k}$ |
| WPC/GA | $6.38 \pm 0.01^{c}$ | $27.60 \pm 0.20^{b}$ | $14.0 \pm 1.7^{jk}$ |
| WPC/GA/*L. plantarum* KLDS 1.0328 | $6.33 \pm 0.01^{d}$ | $28.17 \pm 0.31^{a}$ | $25.0 \pm 1.7^{j}$ |
| MD | $4.77 \pm 0.02^{g}$ | $0.22 \pm 0.01^{k}$ | $215.1 \pm 4.6^{h}$ |
| MD/GA | $4.65 \pm 0.01^{h}$ | $2.02 \pm 0.07^{j}$ | $328.0 \pm 4.6^{d}$ |
| MD/GA/*L. plantarum* KLDS 1.0328 | $4.60 \pm 0.01^{i}$ | $4.56 \pm 0.19^{g}$ | $340.2 \pm 3.1^{c}$ |

NOTE:
in the same column, different lowercase letters indicated that there were significant differences between the samples varying in composition (P < 0.05).

Note: in the same column, different lowercase letters indicated that there were significant differences between the samples varying in composition (P<0.05).

The pH of pure PVOH solution was 7.96±0.02, which was significantly higher than that of other different compositions (P<0.05), followed by pure WPC aqueous solution. In addition, pH of polymer/GA electrospinning and electrospraying solutions compounded with GA were significantly lower than those of the corresponding electrospinning and electrospraying solutions without GA (P<0.05). When *L. plantarum* KLDS 1.0328 was added, pH of WPC/GA solution and MD/GA solution decreased significantly (P<0.05). However, the pH of PVOH/GA solution or PVP/GA solution in the presence of *L. plantarum* KLDS 1.0328 did not differ significantly from pH of the PVOH/GA solution or PVP/GA solution in the absence of *L. plantarum* KLDS 1.0328 (P>0.05).

For the conductivity of the different electrospinning/electrospraying solutions, the conductivities of pure PVP and MD aqueous solution were the lowest among all samples, were (0.37±0.00) mS/cm and (0.22±0.01) mS/cm, respectively, and the difference between the two conductivities was not significant (P>0.05).

For the viscosity of the different electrospinning/electrospraying solutions, the viscosity of the WPC was in the range of (6.0±0.0) cp to (25.0±1.7) cp, which was significantly lower than that of other samples (P<0.05). In addition, it could be found that for all synthetic polymers and natural polymer MD, the presence of GA significantly improved the conductivity (P<0.05) of the corresponding aqueous solution of the polymers. These results may be attributed to the presence of carboxyl and acidic polysaccharides in the GA structure, resulting in the polyelectrolyte property of GA and weakly acidic nature thereof in solution. In addition, compared to aqueous solution of polymers, the viscosity of polymer solutions with GA added increased significantly (P<0.05), which may be due to the presence of GA as a food hydrocolloid with higher molecular weight in solution and increased interchain entanglement with synthetic or natural biopolymers. In addition, after adding *L. plantarum* KLDS 1.0328 to the mixed solution, the conductivity and viscosity of the various solution matrix were further improved. Among them, the conductivity of WPC/GA/*L. plantarum* KLDS 1.0328 was (28.17±0.31) mS/cm, and the viscosity of PVOH/GA/*L. plantarum* KLDS 1.0328 was (544.0±4.6) cp, which was significantly higher than that of other experimental groups (P<0.05), which may be due to the addition of *L. plantarum* KLDS 1.0328 resulting in the introduction of additional bacterial proteins and ions into electrospinning or electrospraying solutions.

3.2 SEM Analysis

The morphology, mean fiber diameter and corresponding diameter distribution of PVOH-based or PVP-based electrospun fibers under SEM were shown in FIGS. 2A-2F and 2G-2L. From FIGS. 2A and 2G, it could be observed that after electrospinning, the pure PVOH solution produced nanofibers with the mean fiber diameter of about (154.62±58.61) nm, the fiber diameters were normally distributed, and the pure PVOH fibers had a uniform, smooth surface and beadless structure.

Figure 2A:
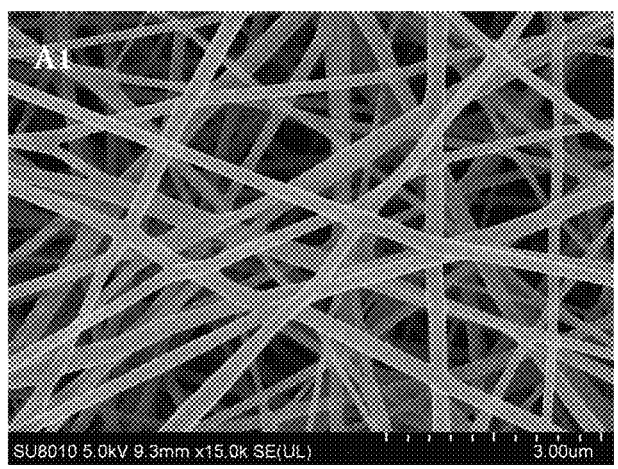
FIGS. 2A-2F are scanning electron microscopy (SEM) images of different electrospun fibers, where 2A: PVOH electrospun fiber; 2B: PVOH/GA electrospun fiber; 2C: PVOH/GA/*L. plantarum* KLDS 1.0328 electrospun fiber; 2D: PVP electrospun fiber; 2E: PVP/GA electrospun fiber; and 2F: PVP/GA/*L. plantarum* KLDS 1.0328 electrospun fiber.
Figure 2B:
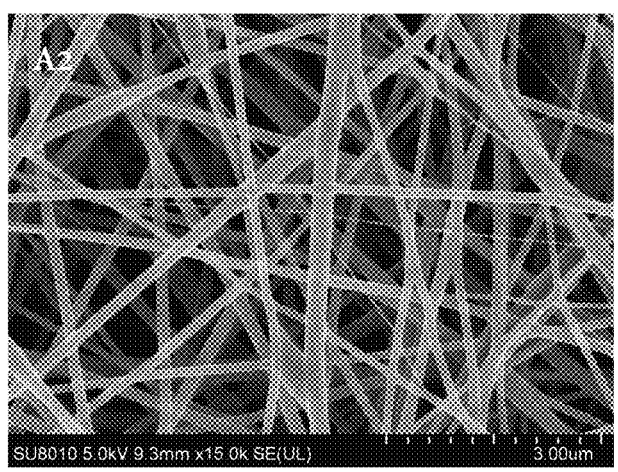
Figure 2C:
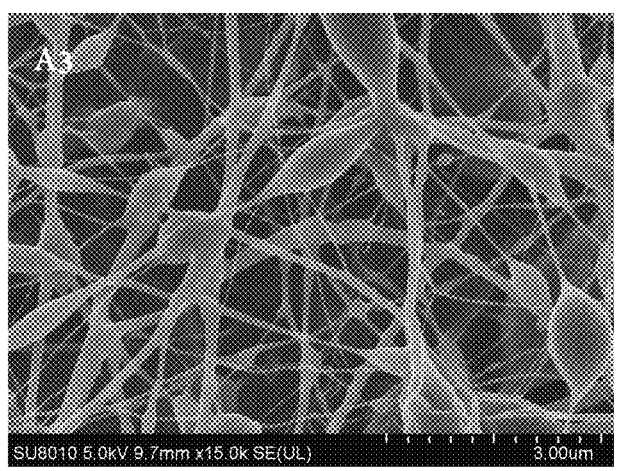
Figure 2D:
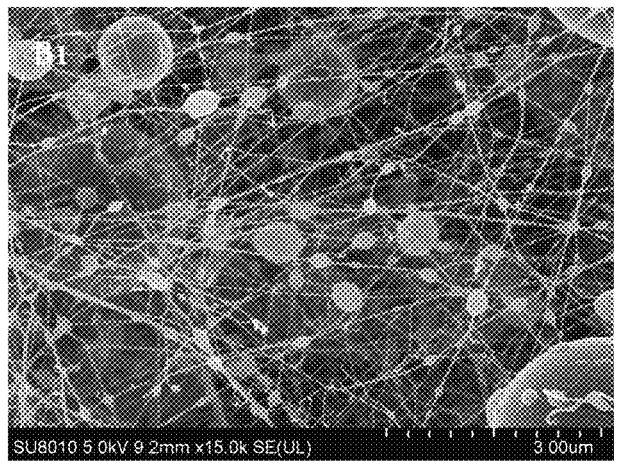
Figure 2E:
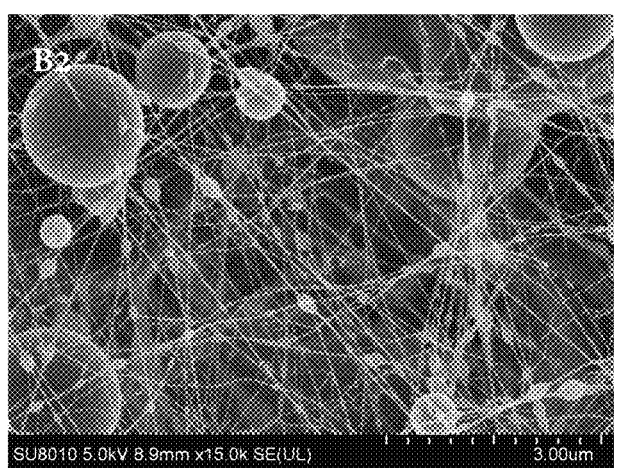
Figure 2F:
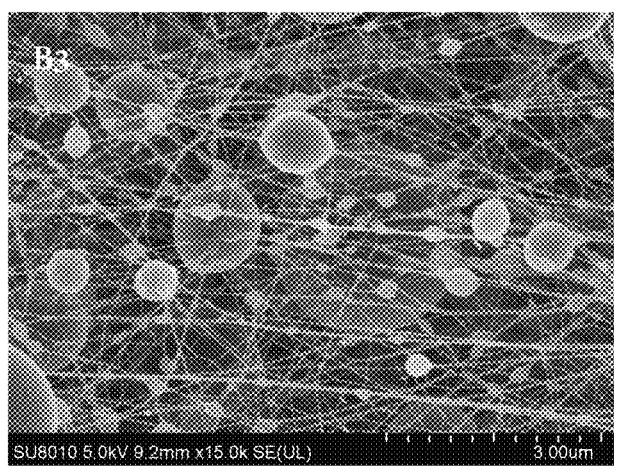
Figure 2G:
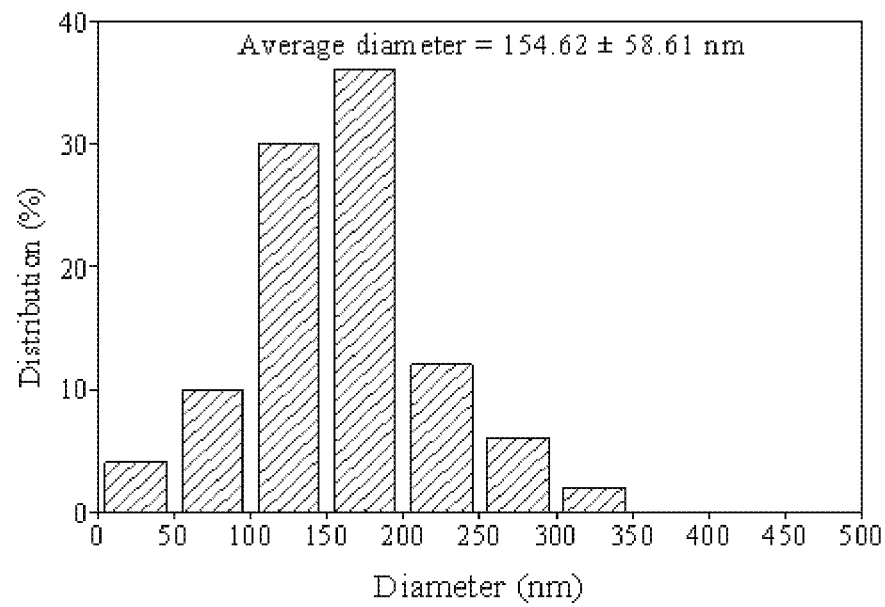
FIGS. 2G-2L show diameter distribution of different electrospun fibers, where 2G: PVOH electrospun fiber; 2H: PVOH/GA electrospun fiber; 2I: PVOH/GA/*L. plantarum* KLDS 1.0328 electrospun fiber; 2J: PVP electrospun fiber; 2K: PVP/GA electrospun fiber; and 2L: PVP/GA/*L. plantarum* KLDS 1.0328 electrospun fiber.
Figure 2H:
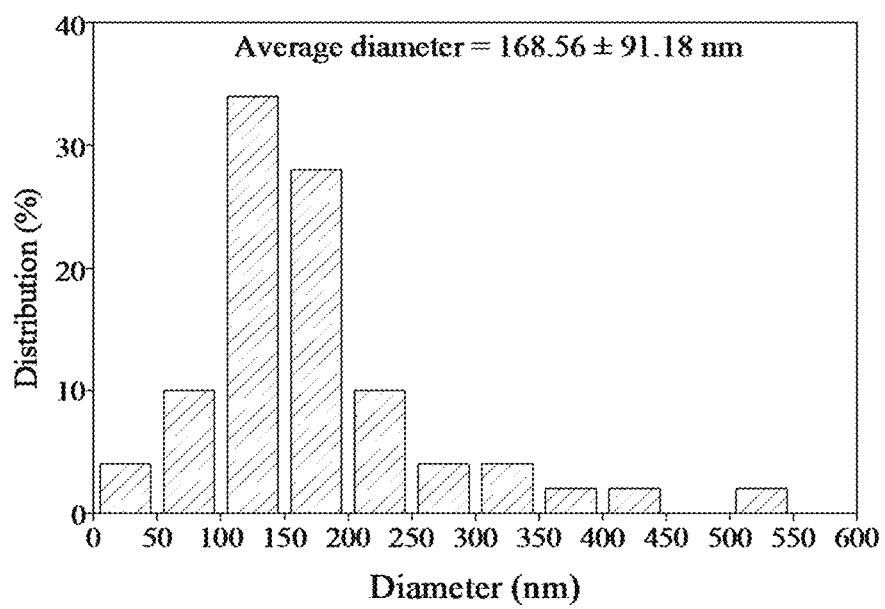

As shown in FIGS. 2B and 2H, when the prebiotics GA was added, it could be seen that the PVOH/GA electrospun fibers were nanofibers with relatively uneven diameters and a few beads, and the average diameter of the fibers was (168.56±91.18) nm, which indicated that PVOH and GA were miscible at the nanoscale. In addition, compared with pure PVOH fibers, PVOH/GA composite solutions produce more microfibers after electrospinning. The morphological change may be related to aforementioned conductivity increase of the solution due to the ionic properties of GA, which increased the electrostatic repulsion between the charges on the jet surface during electrospinning EHD process, further leading to the formation of ultrafine nanofibers.

Figure 2I:
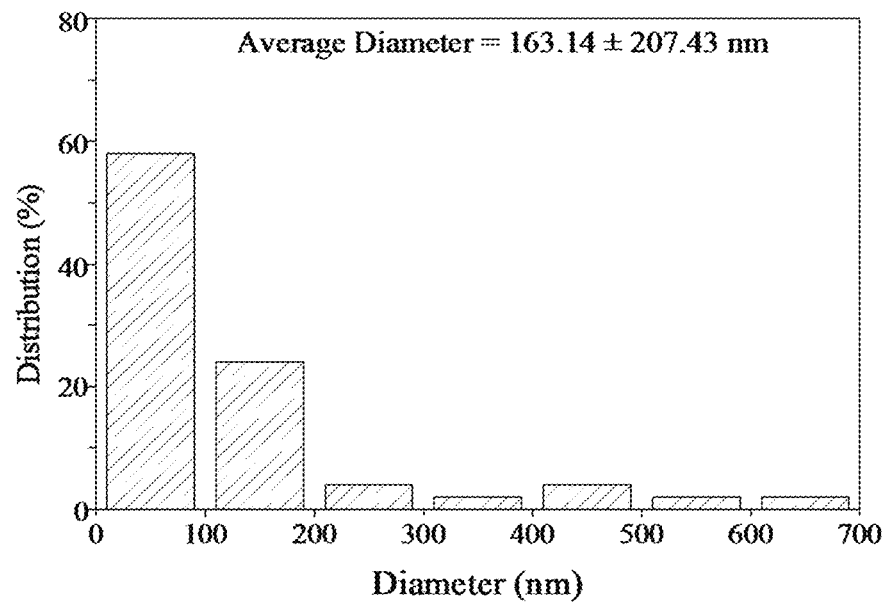
Figure 2J:
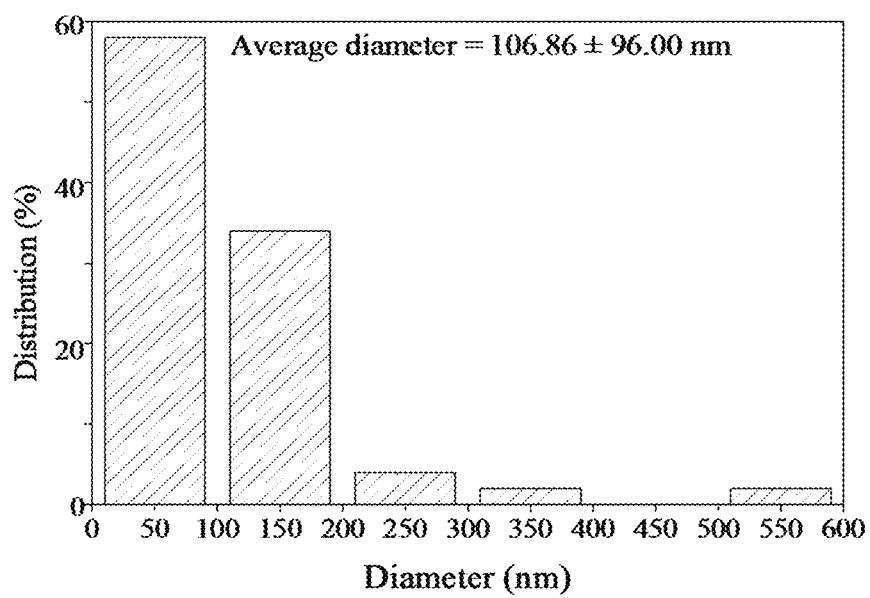
Figure 2K:
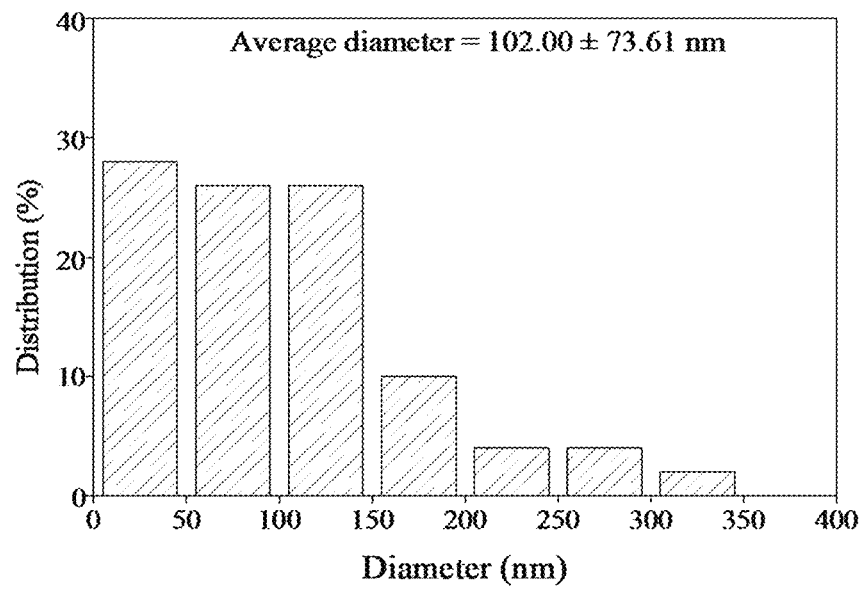
Figure 2L:
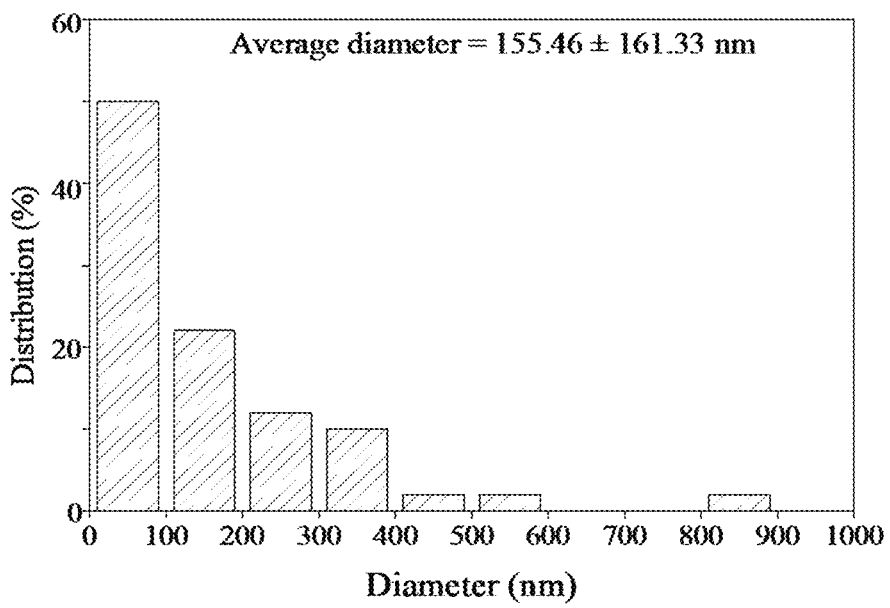
Figure 3A:
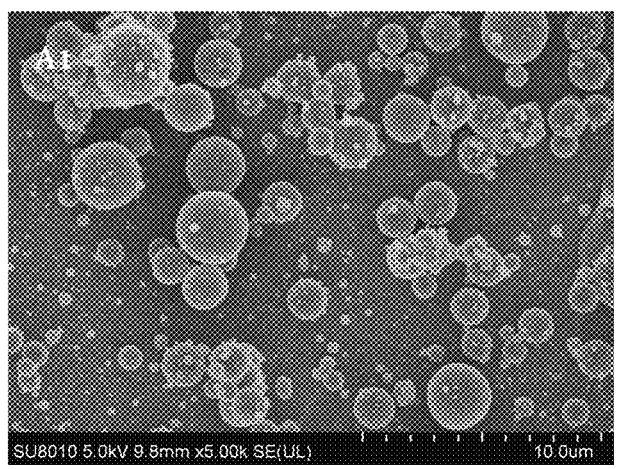
FIGS. 3A-3F are SEM images of different electrosprayed capsules, where 3A: whey protein concentrate (WPC) electrosprayed capsule; 3B: WPC/GA electrosprayed capsule; 3C: WPC/GA/*L. plantarum* KLDS 1.0328 electrosprayed capsule; 3D: maltodextrin (MD) electrosprayed capsule; 3E: MD/GA electrosprayed capsule; and 3F: MD/GA/*L. plantarum* KLDS 1.0328 electrosprayed capsule.
Figure 3B:
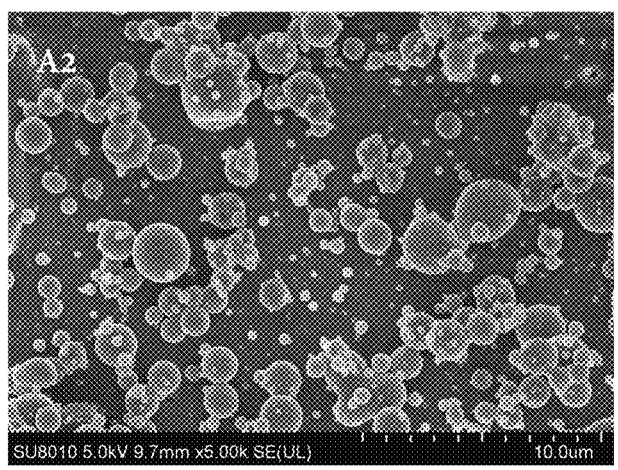
Figure 3C:
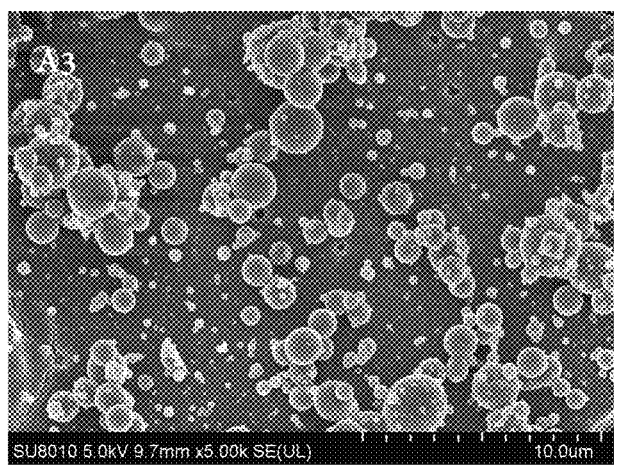
Figure 3D:
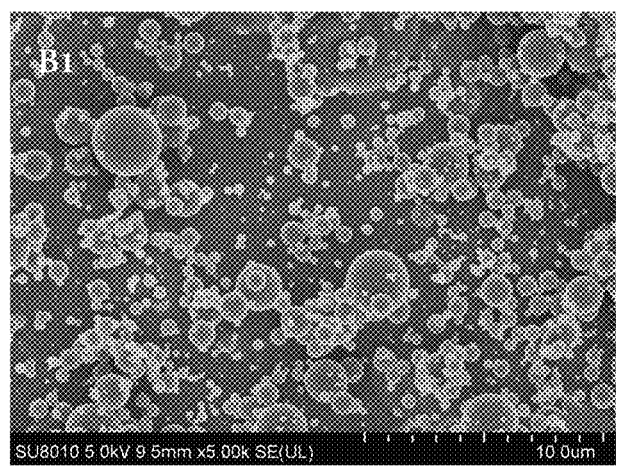
Figure 3E:
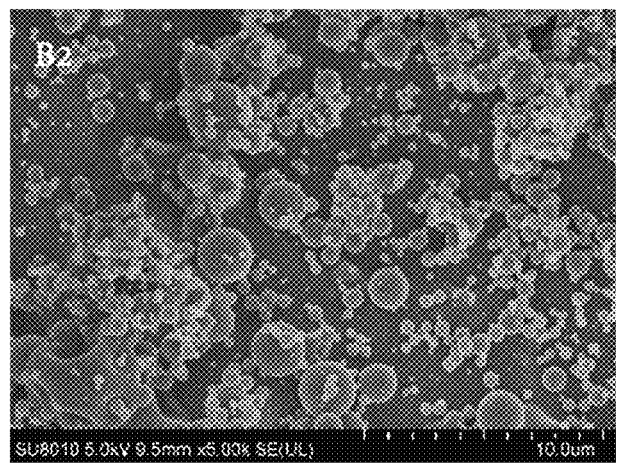
Figure 3F:
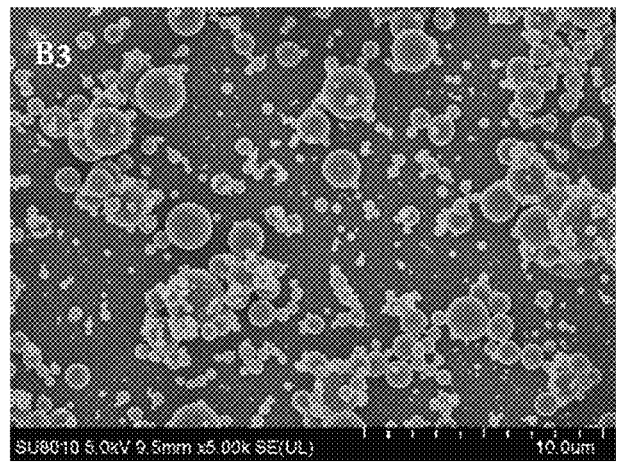
Figure 3G:
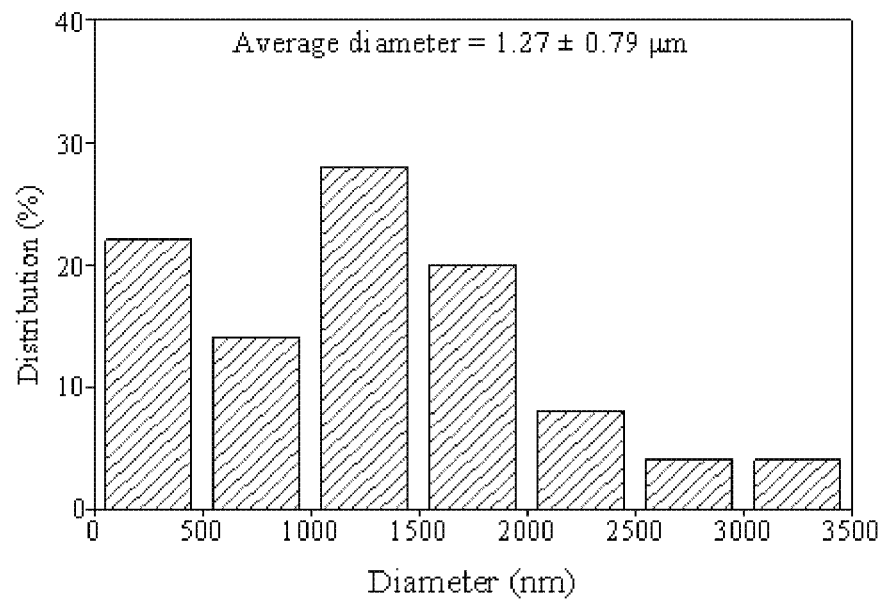
FIGS. 3G-3L show diameter distribution of different electrosprayed capsules, where 3G: WPC electrosprayed capsule; 3H: WPC/GA electrosprayed capsule; 3I: WPC/GA/*L. plantarum* KLDS 1.0328 electrosprayed capsule; 3J: maltodextrin (MD) electrosprayed capsule; 3K: MD/GA electrosprayed capsule; and 3L: MD/GA/*L. plantarum* KLDS 1.0328 electrosprayed capsule.
Figure 3H:
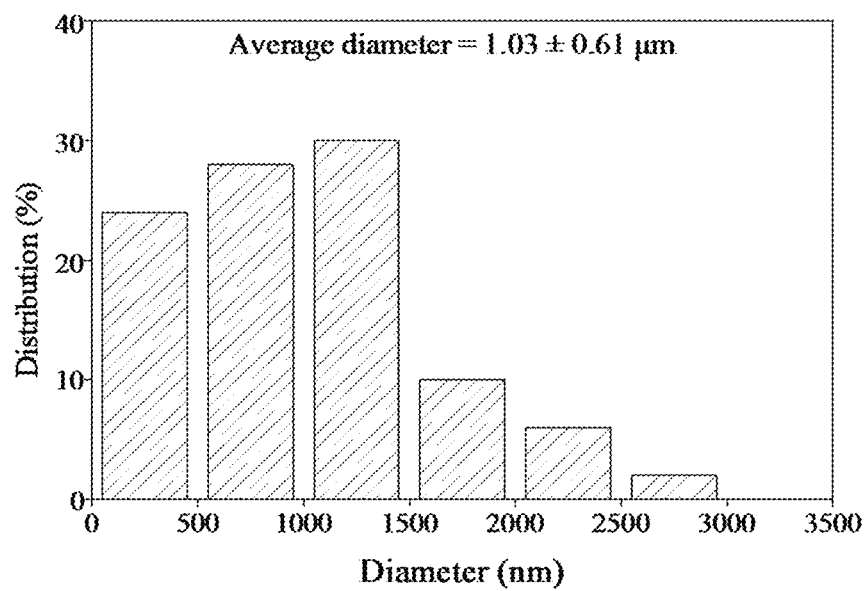
Figure 3I:
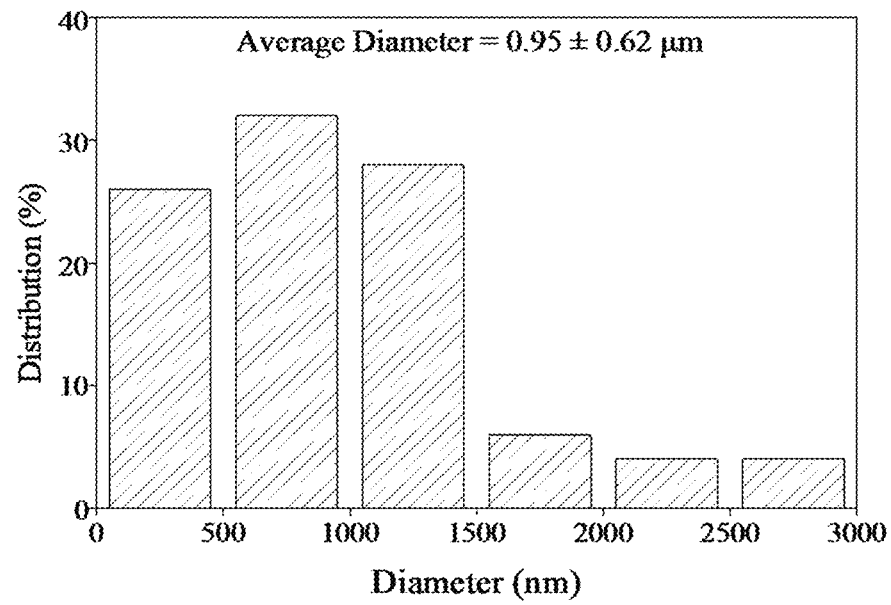
Figure 3J:
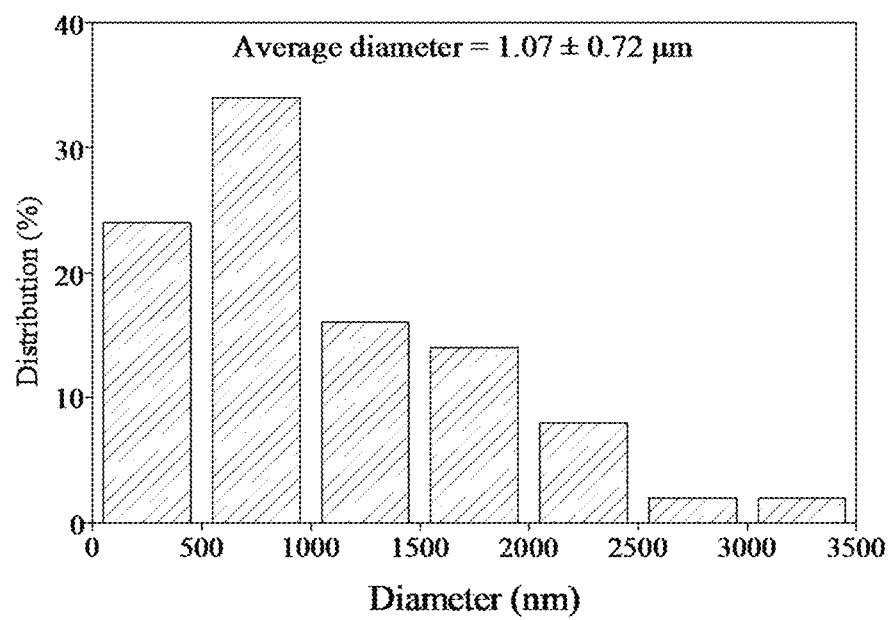
Figure 3K:
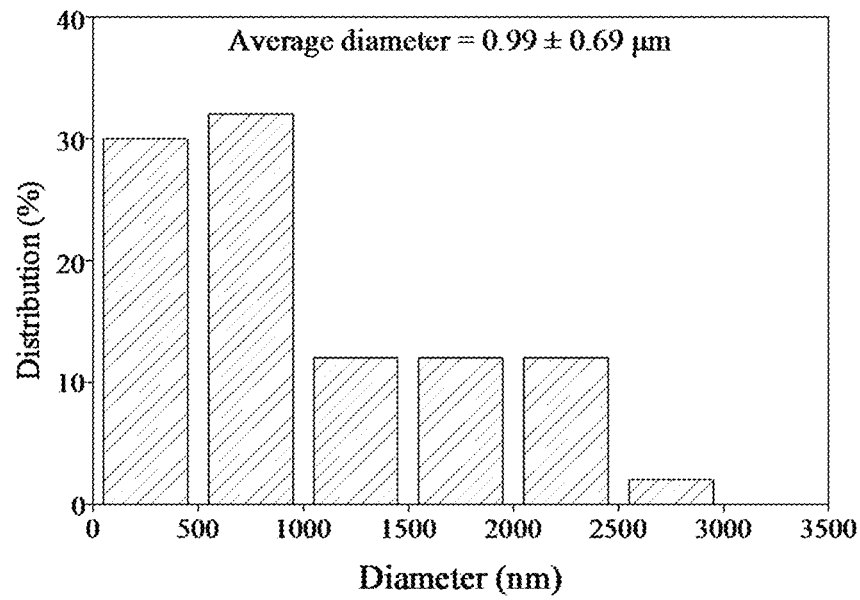
Figure 3L:
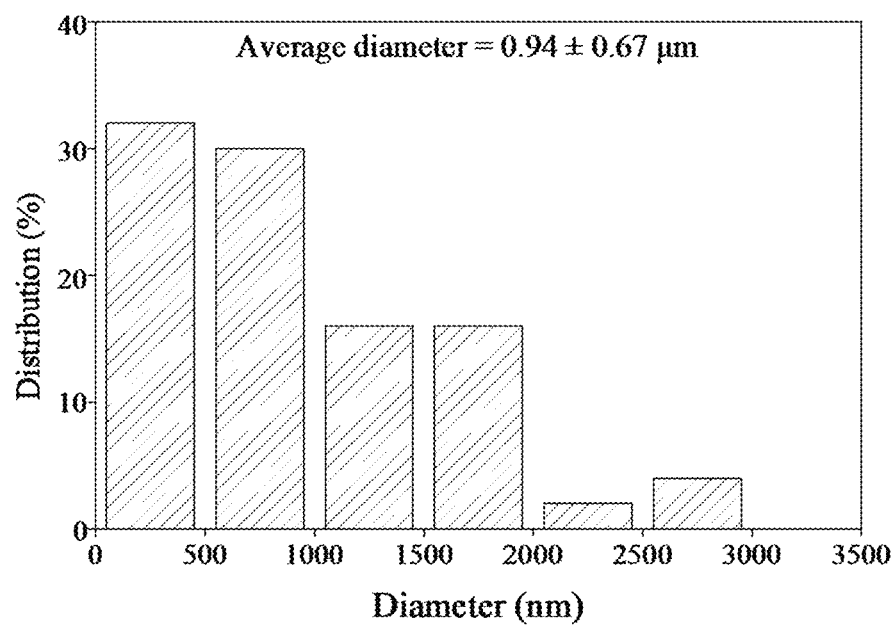

As shown in FIGS. 2C and 2I, the addition of L. plantarum KLDS 1.0328 to the PVOH/GA electrospinning solution did not have a significant effect on the electrospinning process, and PVOH/GA nanofibers encapsulated with L. plantarum KLDS 1.0328 were successfully prepared as expected, but the formation of continuous fibers was impaired to some extent. Nanofibers had some obvious local protrusions and were thickened that the probiotic L. plantarum KLDS 1.0328 had been successfully and directionally incorporated into the PVOH/GA composite nanofiber felt. Combined with the analysis results of the diameter of L. plantarum KLDS 1.0328, it was found that although the diameter of L. plantarum KLDS 1.0328 cells was (0.59±0.04) μm, which was larger than the average diameter of PVOH fibers and PVOH/GA fibers, L. plantarum KLDS 1.0328 cells could still be completely encapsulated with PVOH/GA polymer. L. plantarum KLDS 1.0328 could be oriented along PVOH/GA nanofibers. the bacteria randomly oriented in the polymer solution can start to be oriented at the Taylor cone during electrospinning, mainly along the charged jet, where these bacteria were further arranged in the charged jet, and the jet formed into nanofibers at the end.

For pure PVP, the obtained PVP fibers had an average diameter of about (106.86±96.00) nm and a string of beads thereon. Some droplets or clusters with irregular shape and size, which were not observed in the SEM image of PVOH nanofibers, were formed on PVP electrospinning nanofiber felt. The PVP/GA mixed solution with prebiotic GA formed a material similar to that of PVP fibers by electrospinning, had the mean fiber diameter of about (102.00±73.61) nm, and had many fine beads and large beads. From SEM images, it could be observed that L. plantarum KLDS 1.0328 cells were encapsulated in the PVP/GA nanofibers, which made the ultrafine nanofibers locally widened, and some fibers appeared almost spherical. The significant change in the shape of L. plantarum KLDS 1.0328 during the encapsulation process may result from the instantaneous drying and dewatering at the spinning nozzle and the inevitable high-speed shearing during electrospinning.

The morphology, capsule average diameter and corresponding diameter distribution of WPC-based and MD-based electrosprayed capsules were shown in FIGS. 3A-3F and 3G-3L. Unlike the synthetic polymers (PVOH and PVP), PVOH and PVP mainly formed fibers due to their high molecular weight, while WPC and MD (natural hydrocolloids) presented the form of beads or capsules during the EHD process. From the FIGS. 3A-3F and 3G-3L, it was found that the capsule average diameter of the WPC electrosprayed capsule obtained from pure WPC aqueous solution showed a bimodal distribution, wherein ultra-thin capsules with an average diameter as low as about 200 nm coexisted with some microcapsules with a diameter between 1~3.5 μm in the obtained electrosprayed capsules. In addition, some particle aggregation was observed, which may result from the adsorption of moisture in the environment during the experiment. When WPC was dispersed in the GA solution, the average diameter of capsules was reduced to about (1.03±0.61) μm, and the addition of L. plantarum KLDS 1.0328 further reduced the average diameter of the capsules to (0.95±0.62) μm. Furthermore, the data of the capsule average diameter in both cases were very discrete.

In addition, the microscopic morphology of the MD-based electrosprayed capsules was roughly similar to the WPC-based electrosprayed capsules. The pure MD, MD/GA and MD/GA/L. plantarum KLDS 1.0328 solutions produced, by electrospraying, spherical microcapsule particles with the average diameters of (1.07±0.72) μm, (0.99±0.69) μm and (0.94±0.67) μm, respectively. In addition, in three types of MD-based electrosprayed capsules, particles at the submicron scale (100 nm to 1000 nm) accounted for the largest proportion of all particles. Among them, a small number of spherical particles that appeared to be flattened were obtained from the MD/GA solution, which may be due to particle collapse resulting from solvent evaporation. In addition, a larger diameter distribution was observed for capsules with WPC and MD hydrocolloids as the matrix. The formation of beads instead of fibers in these food hydrocolloids could be attributed to the properties of the polymer solutions described above and the differences in the EHD process. The polymer solution was compounded with GA instead of water as a pure solvent, resulting in a decrease in the average diameter of most biopolymers obtained during EHD process, which may correlate with the conductivity increase of the solution above. This also meant that EHD process could appropriately handle polymer solutions with very different properties such as viscosity, conductivity and surface tension and could have a synergistic effect on the synthesized material. In general, all electrosprayed capsules obtained had an easy-to-handle powdery physical appearance, while the electrospun fibers were presented as continuous fiber mats.

3.3 Fluorescence Microscope Analysis

Figure 4A:
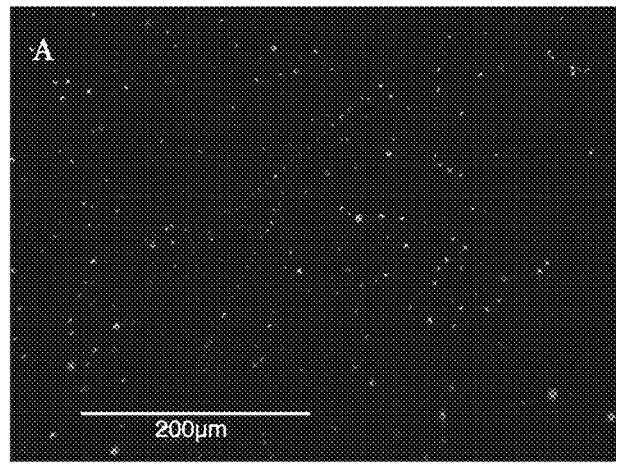
FIGS. 4A-4B are fluorescence microscopy images of rhodamine 123-stained *L. plantarum* KLDS 1.0328 loaded in different electrospun fibers, where 4A: PVOH/GA electrospun fiber; and 4B: PVP/GA electrospun fiber.
Figure 4B:
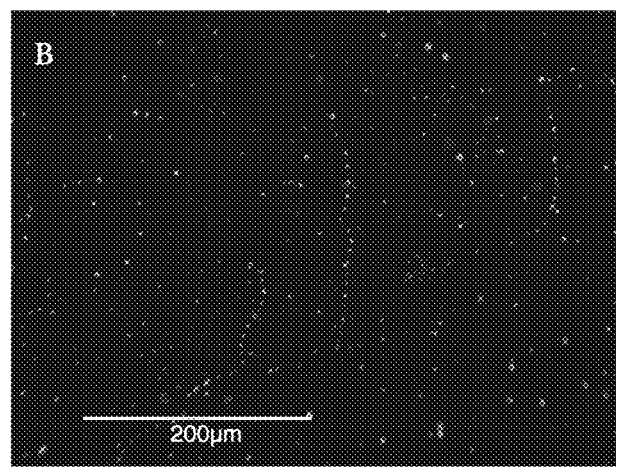
Figure 4C:
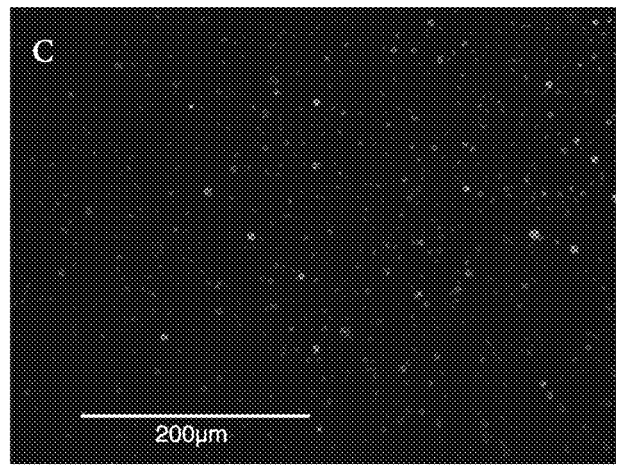
FIGS. 4C-4D are fluorescence microscopy images of rhodamine 123-stained *L. plantarum* KLDS 1.0328 loaded in different electrosprayed capsules, where 4C: WPC/GA electrosprayed capsule; and 4D: MD/GA electrosprayed capsule.
Figure 4D:
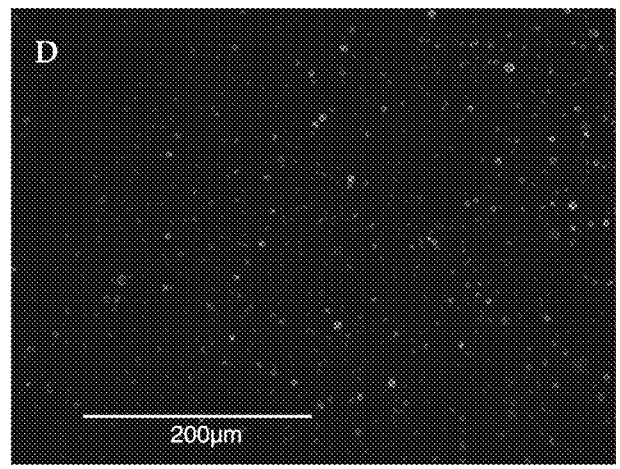

L. plantarum KLDS 1.0328 was stained with the fluorescent dye rhodamine 123, and the electrospinning or electrospraying process was performed in dark environment. Some electrospun fibers and electrosprayed capsules were collected on microscope slides and immediately placed under an inverted fluorescence microscope to confirm the presence and distribution of L. plantarum KLDS 1.0328 cells in the electrospun fibers and electrosprayed capsules. FIGS. 4A-4B are fluorescence microscopy images of rhodamine 123-stained L. plantarum KLDS 1.0328 loaded in different electrospun fibers, where 4A: PVOH/GA electrospun fiber; and 4B: PVP/GA electrospun fiber. FIGS. 4C-4D are fluorescence microscopy images of rhodamine 123-stained L. plantarum KLDS 1.0328 loaded in different electrosprayed capsules, where 4C: WPC/GA electrosprayed capsule; and 4D: MD/GA electrosprayed capsule. Continuous filamentous structure on PVOH/GA and PVP/GA electrospun fibers and green fluorescence appeared in WPC/GA and MD/GA electrosprayed capsules indicated that L. plantarum KLDS 1.0328 was encapsulated in the above structure and could be evenly distributed along the nanofibers or randomly distributed in the particles. This further confirmed that L. plantarum KLDS 1.0328 cells had been efficiently encapsulated.

Figure 5A:
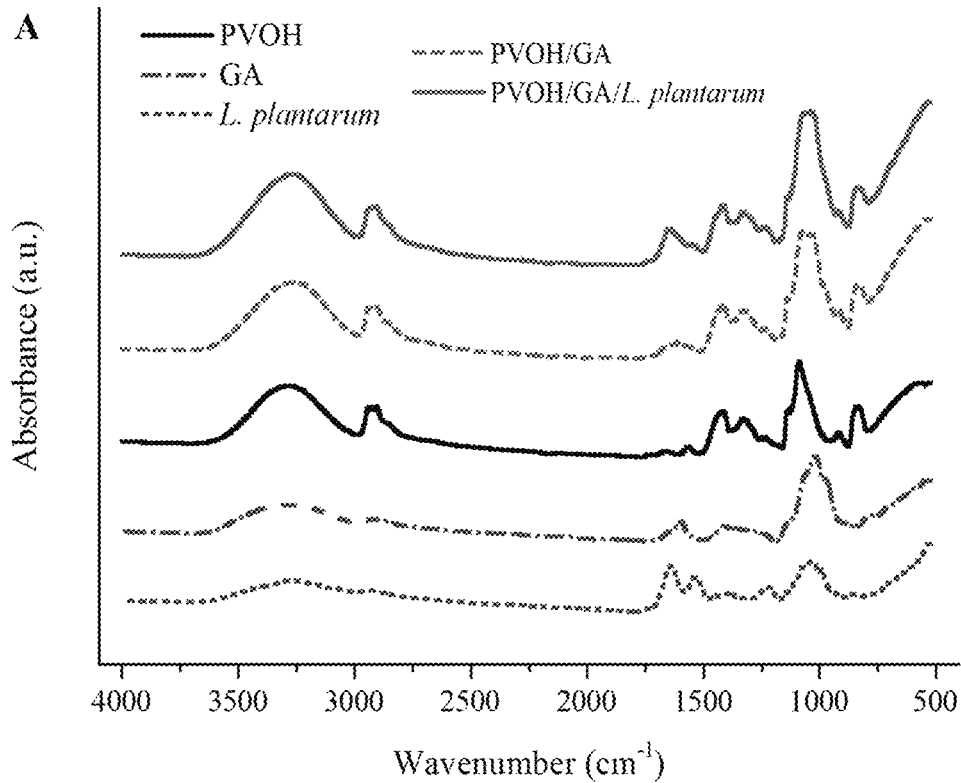
FIGS. 5A-5B are attenuated total reflection-Fourier transform infrared (ATR-FTIR) spectra of electrospun fibers varying in the matrix, where 5A: PVOH-based electrospun fiber; and 5B: PVP-based electrospun fiber.
Figure 5B:
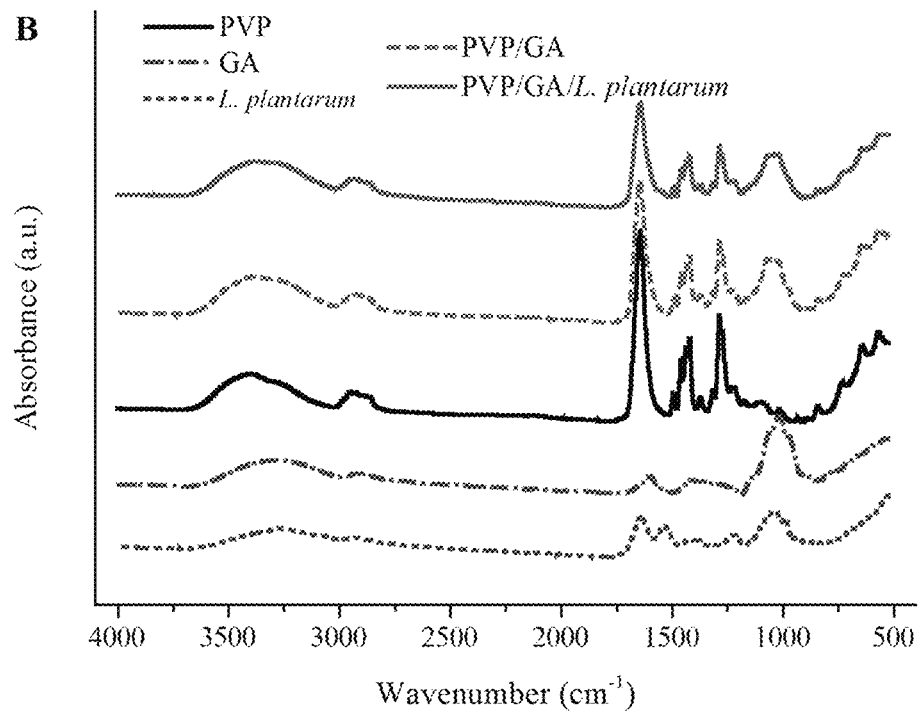

3.4 Attenuated Total Reflection-Fourier Transform Infrared Spectroscopy (ATR-FTIRs) Analysis Infrared spectrograms of the PVOH-based and PVP-based electrospun fibers were respectively presented in FIG. 5A and FIG. 5B. The potential molecular changes in the encapsulation system were identified by ATR-FTIR after L. plantarum KLDS 1.0328 was loaded.

Referring to the infrared spectrum of PVOH-based electrospun fiber in FIG. 5A, the broad band near 3284 cm$^{-1}$ could be attributed to the intramolecular and intermolecular stretching vibration of O—H groups in PVOH; the characteristic peaks observed at 2935 cm$^{-1}$ and 2908 cm$^{-1}$ could be attributed to the asymmetrical stretching vibration of the CH$_2$ group in PVOH; the vibration band near 1417 cm$^{-1}$ could be attributed to the bending vibration of the CH$_2$ group in PVOH, and the peak at 1088 cm$^{-1}$ could be assigned to stretching vibration of C—O and bending vibration of O—H. In addition, the characteristic peak observed at 837 cm$^{-1}$ may be attributed to the C—C vibration.

In the ATR-FTIR spectra of GA powder, the characteristic absorption peak at 3281 cm$^{-1}$ was related to the stretching vibration of O—H and N—H in the amide A region; the absorption peaks at 2922 cm$^{-1}$ and 1601 cm$^{-1}$ matched the asymmetric stretching vibration of C—H and the stretching vibration of C=O or the bending vibration of N—H in the amide I region, respectively. Previous studies had found that the vibration band between 1200 cm$^{-1}$ and 950 cm$^{-1}$ corresponded to C—O—C, C—O—H, and —OH on the pyranose ring, which indicated the presence of pyranose in the GA-PVOH composite. In the presence of GA as a prebiotic, the characteristic absorption peaks attributed to carboxylate anion (—COO$^-$) in the GA molecules could be identified in the infrared spectrum of the blank PVOH/GA composite fiber membrane and the *L. plantarum* KLDS 1.0328-loaded PVOH/GA composite fiber membrane. With respect to the infrared spectrograms of PVOH (3284 cm$^{-1}$), GA (3281 cm$^{-1}$) and *L. plantarum* KLDS 1.0328 (3270 cm$^{-1}$), red shift was observed in the characteristic peak of the O—H stretching vibration in the spectra of PVOH/GA composite electrospun fiber membrane (3265 cm$^{-1}$) and PVOH/GA/*L. plantarum* KLDS 1.0328 electrospun fiber membrane (3267 cm$^{-1}$), which may be explained by the formation of more hydrogen bonds between PVOH, GA, and *L. plantarum* KLDS 1.0328.

ATR-FTIR spectrums of PVP-based electrospun fiber were shown in FIG. 5B, the broad band around 3404 cm$^{-1}$ could be attributed to the stretching vibration of O—H. The absorption peak around 2951 cm$^{-1}$ was caused by the stretching vibration of C—H. The sharp band at 1644 cm$^{-1}$ was the characteristic absorption peak of amide (C=ONH$_2$); Other characteristic absorption peaks of PVP appeared at 1461 cm$^{-1}$ and 1287 cm$^{-1}$, respectively, corresponding to the stretching vibration of C=C and C—N bonds, respectively.

When GA was mixed with the PVP matrix, the absorption band around 3404 cm$^{-1}$ shifted to a lower frequency around 3382 cm$^{-1}$. On one hand, this indicated that the prepared PVP may retain a certain amount of water after undergoing the electrospinning process. On the other hand, due to the high hydrophilicity of PVP with free water molecules and polymer GA, intramolecular and intermolecular hydrogen bonding could be formed in biopolymer chains. In addition, in the infrared spectrum of PVP/GA composite electrospun fibers, the absorption band in the range of 3660 cm$^{-1}$-3100 cm$^{-1}$ associated with the stretching vibration of O—H showed shoulder peaks, and two different absorption peaks near 3382 cm$^{-1}$ and 3295 cm$^{-1}$ indicated that different water was adsorbed, which may be due to the fact that PVP and GA were both hydrophilic polymers and had strong adsorption capacity for water molecules. In addition, due to the combination of GA to PVP matrix, a new strong absorption peak of PVP/GA composite fiber appeared at about 1069 cm$^{-1}$ which corresponded to GA; and a new absorption peak appeared at about 1033 cm$^{-1}$ of PVP/GA composite fiber encapsulated with *L. plantarum* KLDS 1.0328, which corresponded to *L. plantarum* KLDS 1.0328. The previous studies had revealed that regarding the infrared spectra of *Lactobacillus plantarum*, the absorption peak in the wavelength range of 1300 cm$^{-1}$-900 cm$^{-1}$ can be attributed to the protein and nucleic acid of *Lactobacillus plantarum*.

Figure 6A:
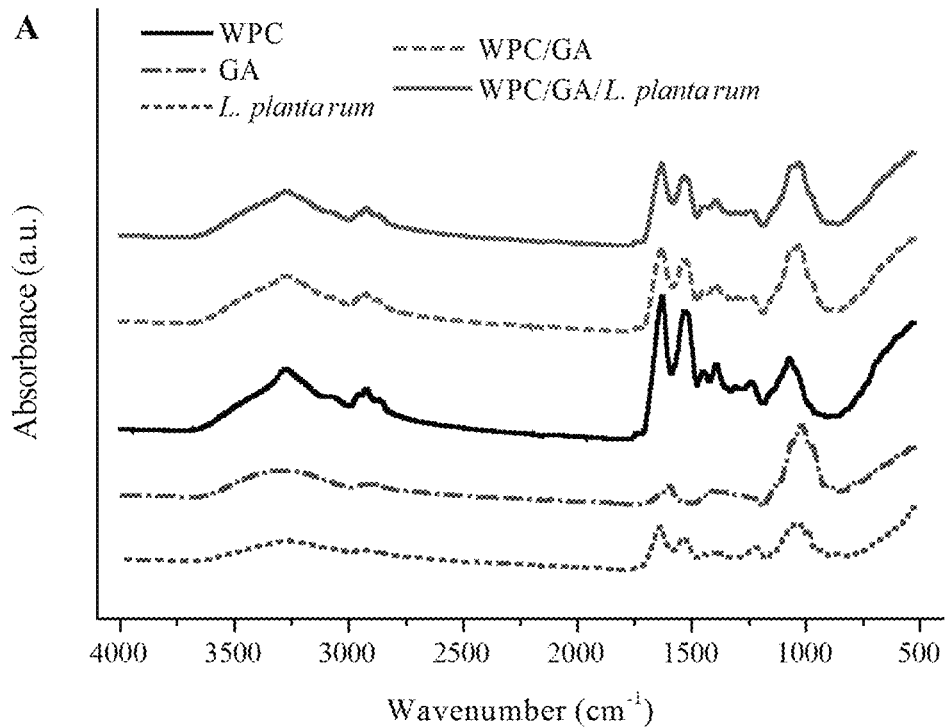
FIGS. 6A-6B are ATR-FTIR spectra of electrosprayed capsules varying in the matrix, where 6A: WPC-based electrosprayed capsule; and 6B: MD-based electrosprayed capsule.
Figure 6B:
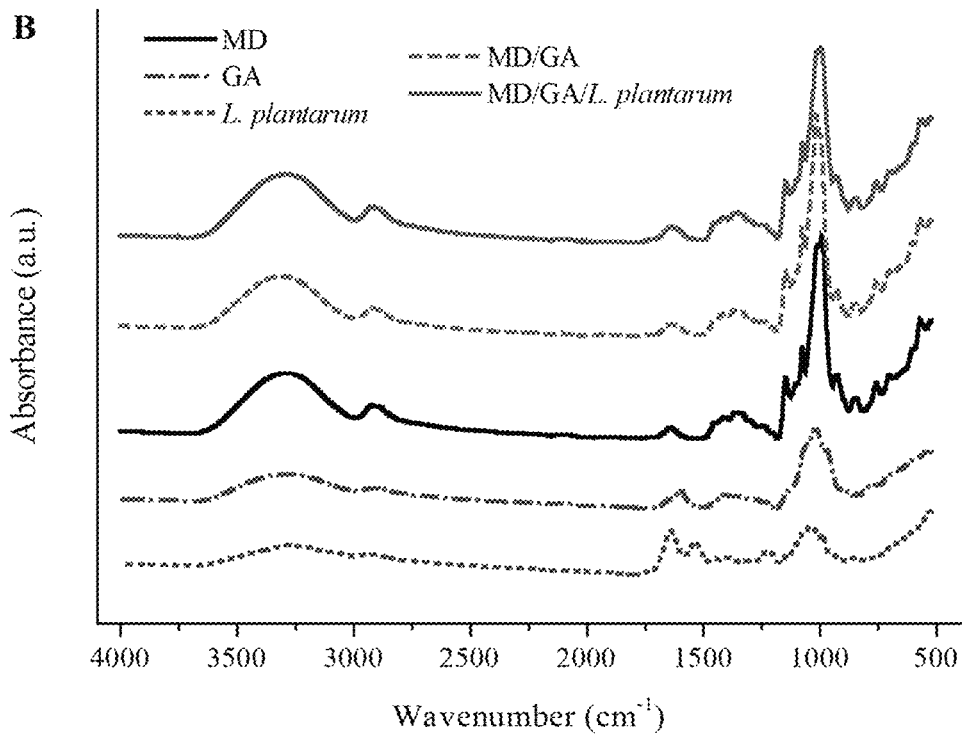

ATR-FTIR spectrograms of the WPC-based and MD-based electrosprayed capsules are respectively presented in FIGS. 6A and 6B. For WPC-based electrosprayed capsules, the addition of GA led to a decrease in the relative intensity of the O—H characteristic band in the infrared spectrum of WPC/GA composite electrosprayed capsules, accompanied by a slight displacement in the vibration frequency from 3274 cm$^{-1}$ to 3271 cm$^{-1}$ (about 3 cm$^{-1}$), which provided evidence for the formation of hydrogen bonds between the polysaccharide GA and the —OH and —NH$_2$ end groups of the protein WPC. The amide I band and amide II band of WPC electrosprayed capsules appeared at 1628 cm$^{-1}$ and 1531 cm$^{-1}$, respectively. When GA was added to the WPC matrix, compared with WPC electrosprayed capsules, the position of the characteristic peak of amide I band (1628 cm$^{-1}$) of the obtained WPC/GA composite electrosprayed capsules did not change significantly, while the characteristic peak of amide II band (1537 cm$^{-1}$) showed blue shift, that was, the wavenumber increased, which resulted from N—H bending vibration and C—N stretching vibration, which had conformational sensitivity. The relative strength of characteristic peaks of amide I band and amide II band in the infrared spectrum of protein WPC was significantly weakened. In addition, a new set of C—O stretching vibration bands appeared at about 1031 cm$^{-1}$, which may be related to the pyranose ring in GA. When *L. plantarum* KLDS 1.0328 was encapsulated in WPC/GA composite electrosprayed capsules, the characteristic absorption peak of 1700 cm$^{-1}$-1500 cm$^{-1}$ presented in WPC/GA electrosprayed capsules caused the overlap of *L. plantarum* KLDS 1.0328 characteristic spectral information. Overall, the infrared spectrum of WPC/GA was very similar to that of WPC/GA/*L. plantarum* KLDS 1.0328. The presence of probiotics within WPC nanoparticles may have little effect on the infrared spectra, possibly due to the relatively small weight percentage of probiotics relative to the encapsulation matrix.

The absorption bands shown in the infrared spectrum of the pristine MD electrosprayed capsules were 3286 cm$^{-1}$ (O—H stretching vibration), 2924 cm$^{-1}$ (C—H stretching vibration), 1640 cm$^{-1}$ (C—O stretching vibration), 1410 cm$^{-1}$ (CH$_2$ bending vibration), 1355 cm$^{-1}$ (O—H bending vibration), 1147 cm$^{-1}$, 1077 cm$^{-1}$, 1012 cm$^{-1}$ and 993 cm$^{-1}$ (C—O stretching vibration and C—O—H bending vibration), 930 cm$^{-1}$, 847 cm$^{-1}$, 759 cm$^{-1}$ and 570 cm$^{-1}$ (skeleton vibration of pyran rings). When GA was added to the MD matrix, the O—H stretching vibration frequency (3316 cm$^{-1}$) of the obtained MD/GA electrosprayed capsule moved to high frequency; after encapsulating *L. plantarum* KLDS 1.0328, the O—H stretching vibration frequency (3316 cm$^{-1}$) of the obtained MD/GA electrosprayed capsule moved towards low frequency to 3286 cm$^{-1}$. These changes indicated a complex interaction between MD, prebiotic GA and *L. plantarum* KLDS 1.0328. In summary, these changes in the infrared spectrum confirmed the successful encapsulation of *L. plantarum* KLDS 1.0328 in a variety of biopolymer matrix, which have been supported by SEM and fluorescence microscope images of the composite electrospun fibers and electrosprayed capsules.

3.5 Analysis of Thermal Properties

Thermogravimetric analysis (TGA) curves and the derivative thermogravimetric (DTG) curves of the PVOH-based and PVP-based electrospun fibers were shown in FIGS. 7A-7B and 7C-7D, respectively. Thermogravimetric analysis (TGA) curves and the derivative thermogravimetric (DTG) curves of WPC-based and MD-based electrosprayed capsules were shown in FIGS. 8A-8B and 8C-8D, respectively. Due to the wide temperature change range corresponding to the weight loss process of some materials, it was difficult to completely identify the thermal properties only by the TGA curves, and the DTG curves can solve the problem. TGA and DTG could characterize the thermal stability of different samples. Since L. plantarum KLDS 1.0328 was encapsulated, the TGA and DTG curves would change compared with the corresponding pure composition, so it was also possible to evaluate whether L. plantarum KLDS 1.0328 was successfully encapsulated through TGA and DTG curves. For the different compositions, and the electrospun fiber and electrosprayed capsule samples prepared, the first weight loss stage below 100° C. was mainly caused by the evaporation of water in each sample. The peaks on the DTG curves represented the fastest loss rate of weight of the samples, and the corresponding peak temperature was the decomposition temperature of the samples. Combined with the TGA and DTG curves of pure GA powder, it could be found that the thermal decomposition temperature of GA was at 304.79° C., at which time galactose, arabinose and rhamnose in the GA structure decomposed. In addition, L. plantarum KLDS 1.0328 had three weightless peaks at 54.11° C., 266.81° C. and 320.14° C., proving that its degradation was mainly carried out in three stages.

Figure 7A:
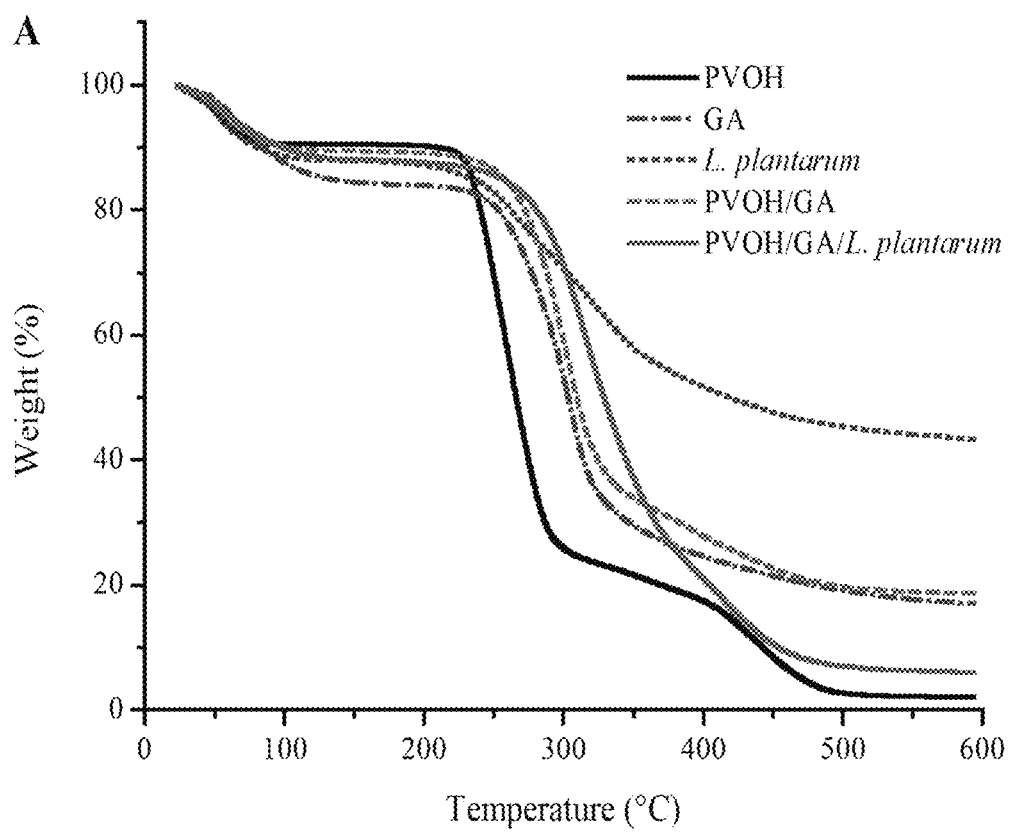
FIGS. 7A-7B show thermogravimetric analysis (TGA) curves of electrospun fibers varying in the matrix, where 7A: PVOH-based electrospun fiber; and 7B: PVP-based electrospun fiber.
Figure 7B:
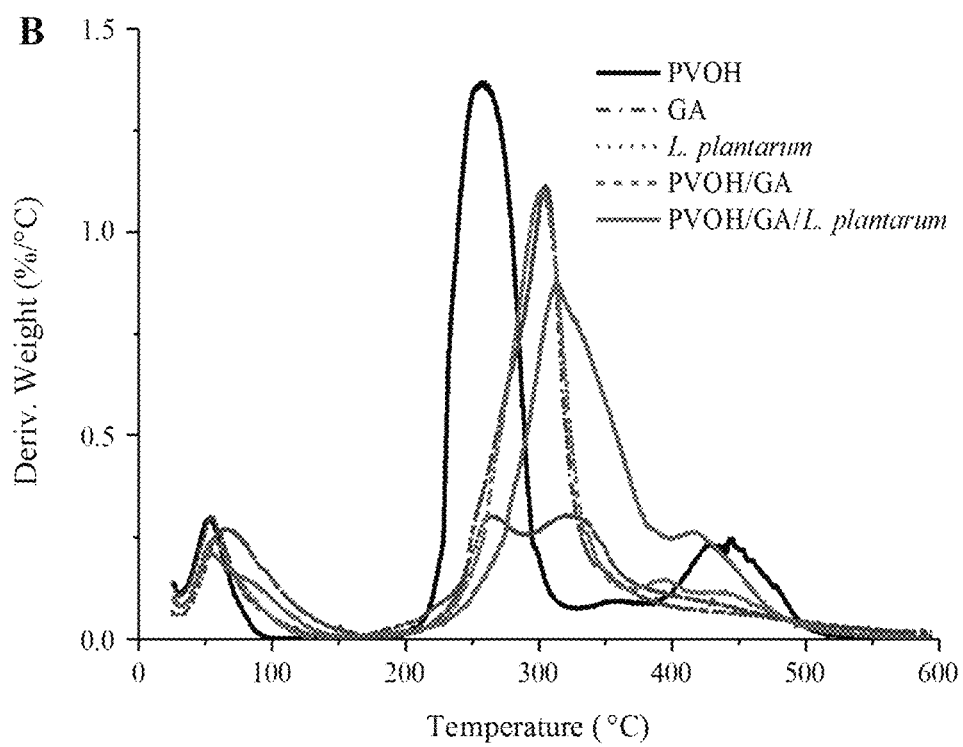
Figure 7C:
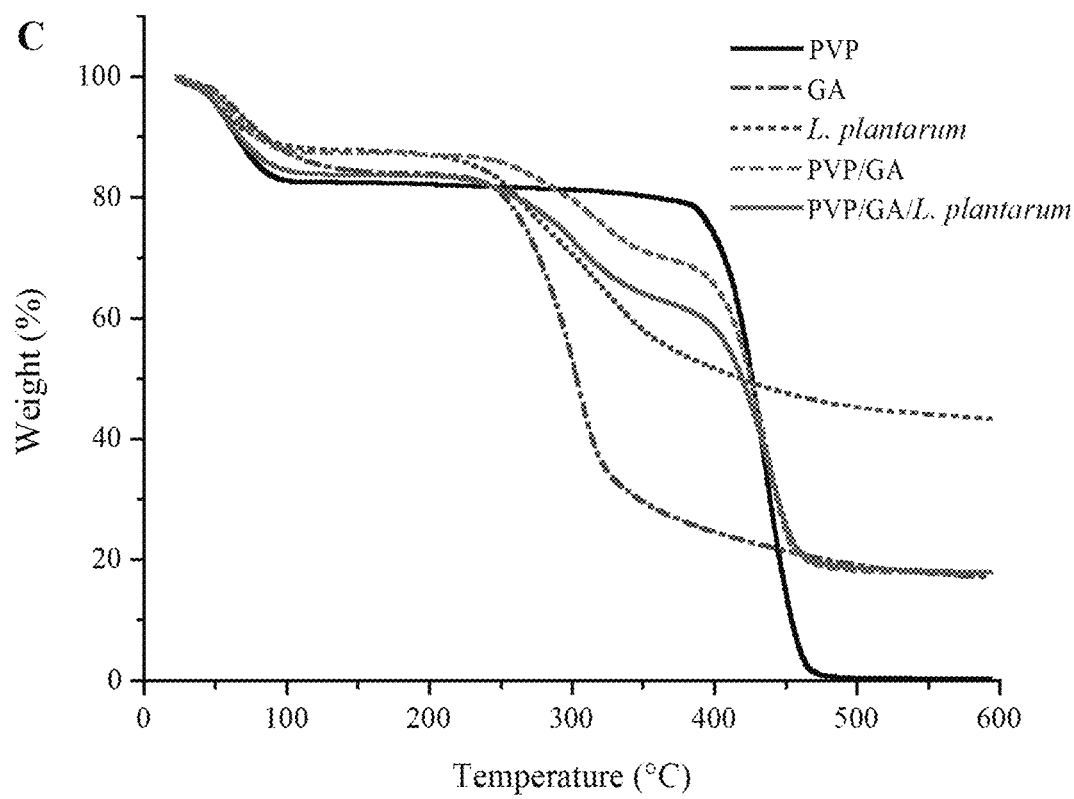
FIGS. 7C-7D show derivative thermogravimetric (DTG) curves of electrospun fibers varying in the matrix, where 7C: PVOH-based electrospun fiber; and 7D: PVP-based electrospun fiber.
Figure 7D:
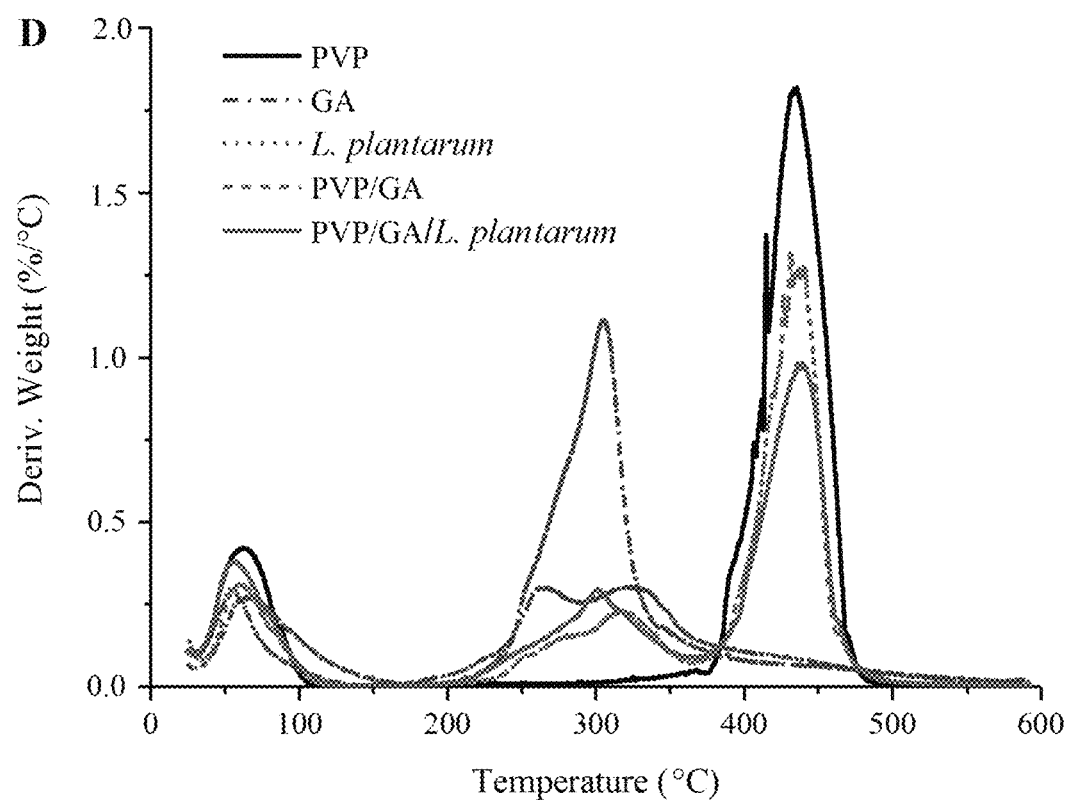
Figure 8A:
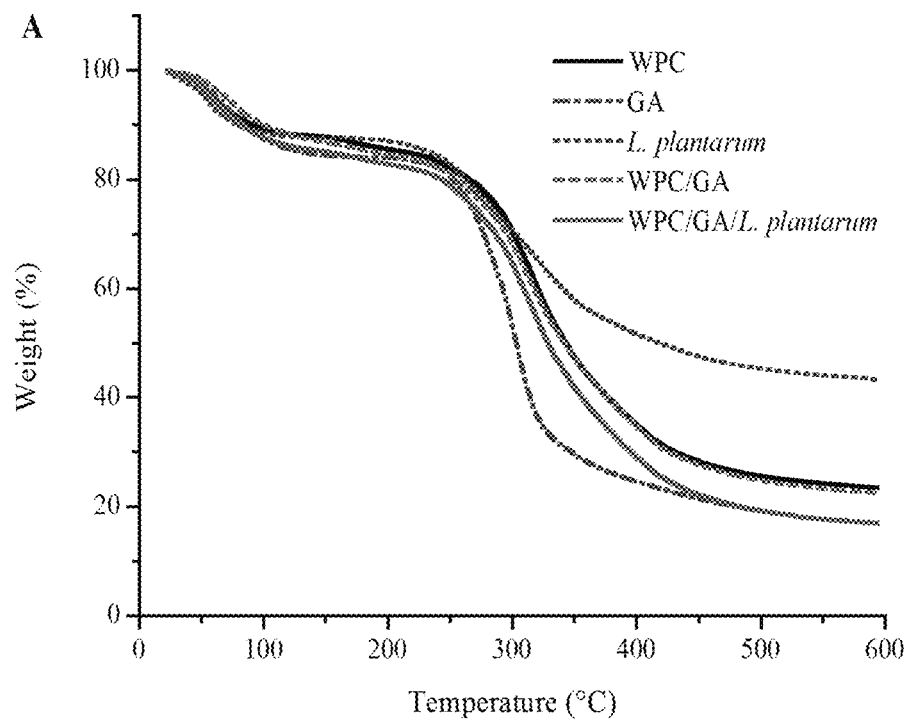
FIGS. 8A-8B show TGA curves of electrosprayed capsules varying in the matrix, where 8A: WPC-based electrosprayed capsule; and 8B: MD-based electrosprayed capsule.
Figure 8B:
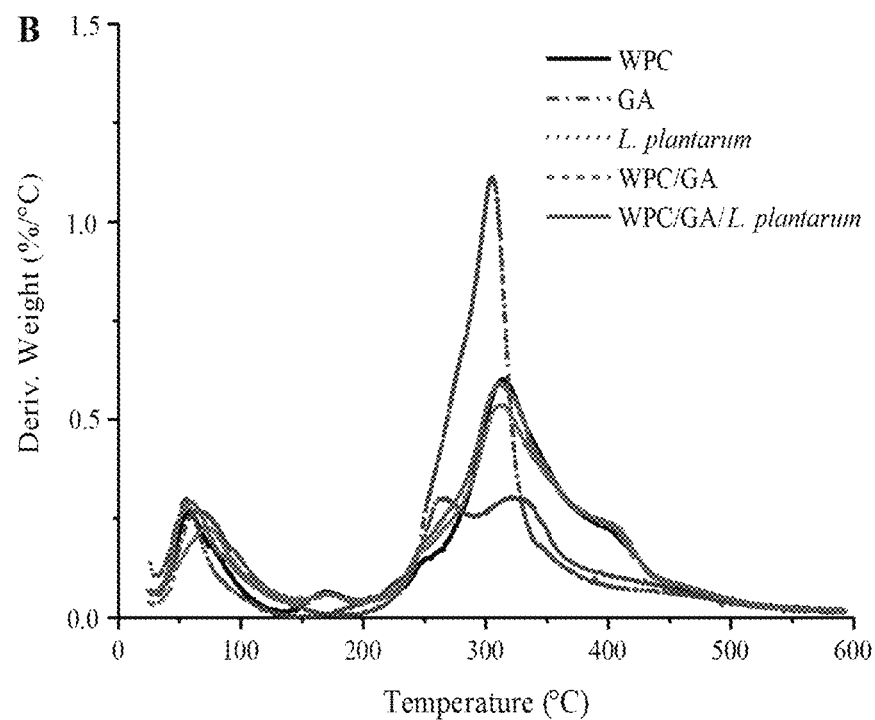
Figure 8C:
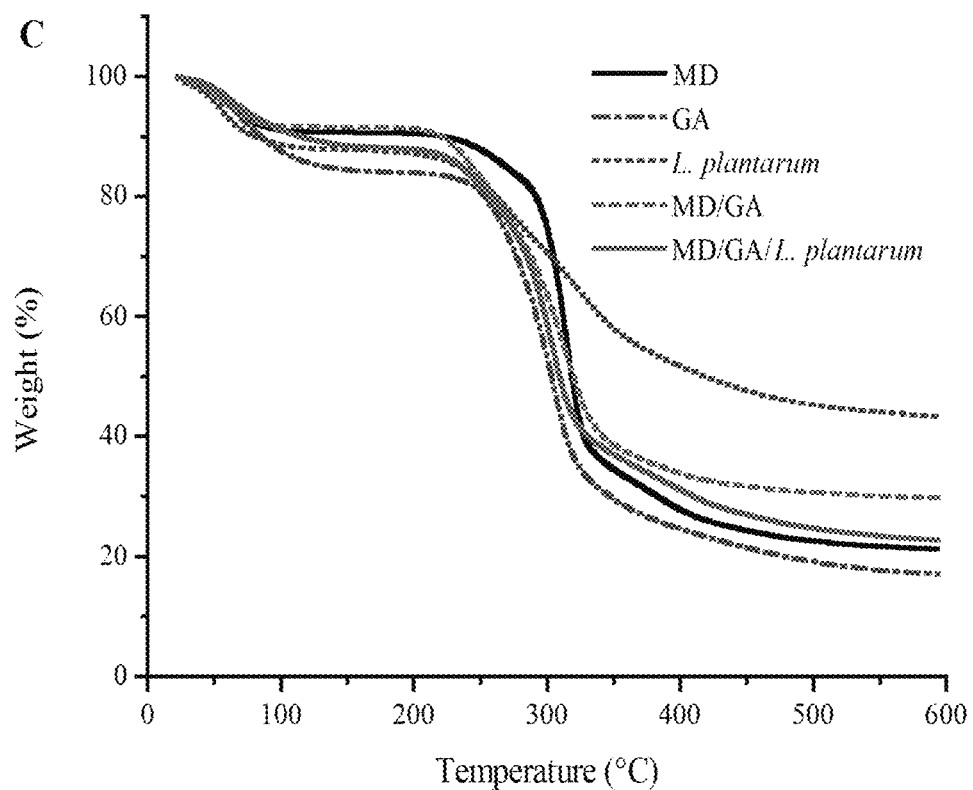
FIGS. 8C-8D show DTG curves of the electrosprayed capsules varying in the matrix, where 8C: WPC-based electrosprayed capsule; and 8D: MD-based electrosprayed capsule.
Figure 8D:
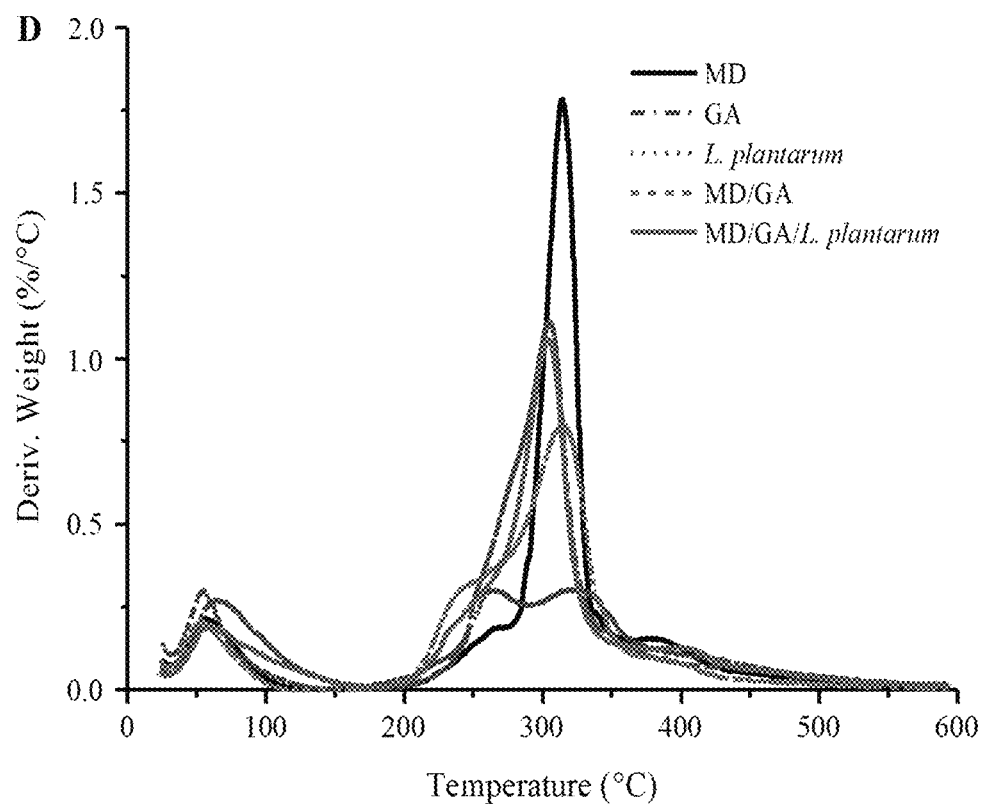

According to FIGS. 7A and 7C, it could be demonstrated that the decomposition of pure PVOH electrospun fibers was carried out in two steps. The decomposition first began at 166.96° C. and continued to 324.02° C., of which, the maximum weight loss rate occurred at 259.22° C., and the decomposition in this stage was mainly due to the chain peeling and chain fracture of PVOH. In the second stage, the significant weight loss occurred at 380~500° C., and the remaining mass fraction at last was about 2%, which was caused by the decomposition and volatilization of the remaining elements in the main chain of the PVOH polymer. It was clearly found that compared with the thermal decomposition temperature (259.22° C.) of pure PVOH electrospun fibers, the addition of GA in PVOH/GA composite electrospun fibers caused the thermal decomposition temperature (302.19° C.) to increase significantly ($P<0.05$), which may be due to the hydrogen bond interaction between PVOH and GA, resulting in an increase in the energy required for the breakage of polymer molecules in the composite film PVOH/GA during heating. The heat resistance of PVOH/GA composite fibers was slightly lower than that of pure GA powder. For the electrospun fibers prepared by pure PVP aqueous solution, about 82% of the weight loss occurred between about 100° C. and 500° C., the mass dropped sharply between 400° C. and 460° C., and the thermal decomposition temperature was 435.41° C. Finally, the overall weight loss rate of pure PVP electrospun fiber was approximately 100%. In addition, the thermal decomposition temperature of PVP/GA (431.23° C.) was slightly lower than that of electrospun fibers prepared by pure PVP, and significantly higher than that of pure GA powder.

As can be seen from FIGS. 8A-8B and 8C-8D, the DTG curves of pure WPC and MD electrosprayed capsules had strong reaction peaks at 313.60° C. and 314.36° C., which were caused by the thermal degradation of WPC and MD, respectively. In particular, between room temperature and 600° C., the natural biopolymer of WPC or MD electrosprayed capsules had less weight loss and better thermal stability than electrospun fibers made from the synthetic biopolymer of PVOH or PVP. In addition, after adding GA to the two natural biological macromolecular systems of WPC and MD, the thermal decomposition curves of WPC/GA or MD/GA electrosprayed capsules were not the simple linear sum of GA and WPC or MD, but showed their unique decomposition performance, and the thermal decomposition temperature of both was slightly lower than that of pure electrosprayed capsules, 311.62° C. and 313.41° C., respectively.

Furthermore, compared with the electrospun fibers prepared by PVOH/GA (302.19° C.) and PVP/GA (431.23° C.), the decomposition temperatures of PVOH/GA/L. plantarum KLDS 1.0328 and PVP/GA/L. plantarum KLDS 1.0328 were significantly increased, reaching 314.59° C. and 438.91° C., respectively ($P<0.05$). This phenomenon could be attributed to the fact that L. plantarum KLDS 1.0328 cells had been wrapped in electrospun fibers. However, for the natural biopolymer WPC and MD, compared with the electrosprayed capsules formed by WPC/GA and MD/GA before the addition of bacteria, the corresponding thermal decomposition temperature of the two electrosprayed capsules encapsulated with L. plantarum KLDS 1.0328 was significantly reduced, and 309.23° C. and 303.43° C. ($P<0.05$), respectively. This may be due to the difference between the electrospinning and electrospraying processes to construct the L. plantarum KLDS 1.0328 carrier, as well as the differences in the different compositions in the encapsulation materials.

3.6 Stress Resistance of the Electrospun Fibers/Electrosprayed Capsules Encapsulated with L. plantarum KLDS 1.0328

(1) Viability of the encapsulated L. plantarum KLDS 1.0328 cells

The viability of L. plantarum KLDS 1.0328 in the electrospinning/electrospraying solutions and the prepared electrospun nanofibers/electrosprayed capsules under SGF and SIF treatment was shown in Table 3. It was found that L. plantarum KLDS 1.0328 retained the activity after encapsulation in all biopolymer solutions, and there was no significant difference in the viable cell count between free L. plantarum KLDS 1.0328 cells and biopolymer solutions ($P<0.05$), which indicated that PVOH, PVP, WPC, MD and their complexes with prebiotic GA had good compatibility with L. plantarum KLDS 1.0328 and could be used to prepare carriers encapsulated with the L. plantarum KLDS 1.0328.

In general, compared with the viable cell count in electrospinning/electrospraying solution before electrospinning and electrospraying processing, the activity of L. plantarum KLDS 1.0328 encapsulated in the electrospun fibers or electrosprayed capsules was generally slightly lower than that of the initial polymer solutions, and there was no significant difference except MD/L. plantarum KLDS 1.0328 ($P<0.05$); and the survival rate of L. plantarum KLDS 1.0328 in the electrospun fibers or electrosprayed capsules formed by each material composition decreased less than 1 lg CFU/g, that was, it showed high survivability. Among them, the encapsulation rate of PVOH/GA electrospun fiber for L. plantarum KLDS 1.0328 was relatively high (96.50±1.14)%. However, the encapsulation rate of pure MD electrosprayed capsules for L. plantarum KLDS 1.0328 was relatively the low (92.98±1.98)%, which indicated that the encapsulation material in the EHD process, that was, the formulation of biopolymers, would affect the encapsulation rate and cell viability to a certain extent. The viability loss of L. plantarum KLDS 1.0328 during the EHD process could attribute to the transient low osmotic stress, shear stress and negative effects of high voltage electric field caused by the rapid evaporation of solvent water during electrospinning or electrospraying. In order to rule out the influence of the direction of the EHD process and the cell viability loss due to gravity, the horizontal device was changed to the vertical direction, and it was found that there was no significant difference in the viability of the bacteria, which indicated that the direction of the EHD process under the experimental conditions had no major effect on the survival rate of *L. plantarum* KLDS 1.0328. Compared with the previous studies, the pullulan and the prebiotic GA was performed with freeze-drying to protect the encapsulation rates of *L. plantarum* KLDS 1.0328, *Lactobacillus acidophilus*, *Lactobacillus rhamnosus* and *Lactobacillus casei* in 80.92~89.84%, and the electrospun fibers or electrosprayed capsules encapsulated with *L. plantarum* KLDS 1.0328 could better protect the encapsulated cells. The formation of ice crystals and cell damage caused by extremely low temperatures may be the cause of the death of the above *lactobacillus* cells during lyophilization, and the EHD process not only used aqueous solutions as solvents but could be carried out quickly and continuously at room temperature without being subjected to too low or high environmental stress, thereby reducing the damage to the viability and function of living cells. In addition, GA, as a dietary fiber with prebiotic properties, could be selectively fermented into short-chain fatty acids by Lactobacilli and Bifidobacteria, and the high solubility could inhibit particle shrinkage and provide higher protection efficiency for *L. plantarum* KLDS 1.0328.

TABLE 3

Viability of *L. plantarum* KLDS 1.0328 in electrospinning/electrospraying solution and synthetic electrospun fiber/electrosprayed capsules under different conditions

| | Viable cell count (lg CFU/g) | | | |
|---|---|---|---|---|
| Samples | Before encapsulation | After encapsulation | After SGF treatment | After SIF treatment |
| Free *L. plantarum* | 9.75 ± 0.04 $^a$ | — | 5.44 ± 0.15 $^f$ | 4.49 ± 0.14 $^g$ |
| PVOH/*L. plantarum* | 9.72 ± 0.05 $^a$ | 9.24 ± 0.05 $^{ab}$ | 7.72 ± 0.14 $^{bc}$ | 7.48 ± 0.08 $^{ab}$ |
| PVOH/GA/*L. plantarum* | 9.87 ± 0.07 $^a$ | 9.38 ± 0.05 $^a$ | 8.16 ± 0.10 $^a$ | 7.63 ± 0.11 $^a$ |
| PVP/*L. plantarum* | 9.80 ± 0.06 $^a$ | 9.23 ± 0.07 $^{ab}$ | 7.31± 0.07 $^d$ | 6.94 ± 0.07 $^d$ |
| PVP/GA/*L. plantarum* | 9.77 ± 0.09 $^a$ | 9.26 ± 0.08 $^{ab}$ | 7.46 ± 0.07 $^{bcd}$ | 7.10 ± 0.13 $^{cd}$ |
| WPC/*L. plantarum* | 9.82 ± 0.13 $^a$ | 9.28 ± 0.03 $^{ab}$ | 7.38 ± 0.08 $^{cd}$ | 6.90 ± 0.06 $^d$ |
| WPC/GA/*L. plantarum* | 9.82 ± 0.06 $^a$ | 9.33 ± 0.11 $^{ab}$ | 7.75 ± 0.14 $^b$ | 7.26 ± 0.09 $^{bc}$ |
| MD/*L. plantarum* | 9.81 ± 0.07 $^a$ | 9.13 ± 0.14 $^b$ | 6.35 ± 0.13 $^e$ | 5.71 ± 0.07 $^f$ |
| MD/GA/*L. plantarum* | 9.79 ± 0.08 $^a$ | 9.15 ± 0.10 $^{ab}$ | 6.55 ± 0.20 $^e$ | 6.38 ± 0.08 $^e$ |

NOTE:
in the same column, different lowercase letters indicated that there were significant differences between the samples varying in composition (P < 0.05)

Note: in the same column, different lowercase letters indicated that there were significant differences between the samples varying in composition (P<0.05)

(2) Tolerance analysis of the free and encapsulated *L. plantarum* KLDS 1.0328 in simulated gastrointestinal tract Digestive resistance was one of the key properties that probiotic foods should have. The viability loss of *L. plantarum* KLDS 1.0328 in the electrospun fiber or electrosprayed capsule and the prebiotic effect of GA on encapsulated *L. plantarum* KLDS 1.0328 after the continuous SGF and SIF treatment were evaluated, as shown in Table 3. It was clearly found that the viability of free *L. plantarum* KLDS 1.0328 cells decreased significantly after exposure to SGF and SIF, and the viable cell count decreased to (5.44±0.15) lg CFU/g and (4.49±0.14) lg CFU/g, respectively, indicating that *L. plantarum* KLDS 1.0328 cells were sensitive to the processing conditions of SGF and SIF in vitro. The results showed that the different kinds of encapsulation materials had different protective action against *L. plantarum* KLDS 1.0328 cells. After 120 min of SGJ treatment, in the control group, the viable cell count of free *L. plantarum* KLDS 1.0328 cells decreased by about 4.30 lg CFU/g, while the viable cell count in PVOH/GA composite electrospun fibers encapsulated with *L. plantarum* KLDS 1.0328 cells decreased by only about 1.22 lg CFU/g. In addition, after 120 min of SGJ treatment, it was found that the viable number of *L. plantarum* KLDS 1.0328 in PVOH/GA composite electrospun fibers was (8.16±0.10) lg CFU/g, which reached the highest viable cell count in each group of the encapsulation materials and was significantly higher than that in pure PVOH fibers (P<0.05), while the viability of the remaining cells decreased slightly in subsequent SIF. PVOH/GA still had the highest level compared to the viable cell count of *L. plantarum* KLDS 1.0328 in other encapsulation materials after exposure to simulated gastrointestinal tract. This may be due to that the microstructure of PVOH/GA composite fibers were denser than that of the pure PVA fibers, as confirmed by infrared spectroscopy that intermolecular hydrogen bonds were formed between the functional groups of PVOH and GA, thereby weakening the adverse effects of the external stress environment. After SGF and SIF treatment, compared with pure WPC electrosprayed capsules, the composite electrosprayed capsules prepared from prebiotics GA and WPC significantly improved the viability of *L. plantarum* KLDS 1.0328 (P<0.05). After SGF treatment, compared with the corresponding PVP electrospun fibers and MD electrosprayed capsules without prebiotic GA, the survival number of *L. plantarum* KLDS 1.0328 in PVP electrospun fibers and MD electrosprayed capsules mixed with prebiotic GA was not significantly different (P>0.05). This may result from that the GA added to the encapsulation material at this time was not enough as a nutritional and energy source for *L. plantarum* KLDS 1.0328, and it was relatively difficult to improve the stability of probiotics in the SGF stress environment. In addition, it was found that the *L. plantarum* KLDS 1.0328 cells encapsulated in pure MD and MD/GA electrosprayed capsules had a large relative loss of viability, which indicated that MD and MD/GA electrospraying materials had a low protective effect on the cells compared with other encapsulation materials, which may be due to the loose structure of MD electrosprayed capsules, and the protective effect on cells when suspended in SGF and SIF was relatively weak. Previous studies have shown that some traditional carbohydrates such as maltodextrin and starch may not be considered suitable protectors against digestive juices. In this experiment, MD and MD/GA electrosprayed capsules could significantly improve the tolerability of *L. plantarum* KLDS 1.0328 (P<0.05) in vitro simulated gastrointestinal environment compared with unencapsulated free *L. plantarum* KLDS 1.0328, and the final viable number was still higher than the viable cell count ($10^6$ CFU/g) required by probiotic health foods. The continuous gastrointestinal simulation test in vitro further verified that a variety of the electrospun fibers or electrosprayed capsules prepared by the EHD process optimized by this experiment, especially when PVOH and WPC were used as substrates and supplemented by prebiotic GA, which could better protect the vitality of *L. plantarum* KLDS 1.0328.

(3) Analysis of the tolerance of free and encapsulated *L. plantarum* KLDS 1.0328 under different osmotic stress and humidity and heat stress In food processing, NaCl content was an important factor affecting the viability of probiotics. In addition, the osmotic stress change due to the change of ionic strength may also destroy the protective structure of the biopolymer formed by electrospinning or electrospraying process. The effects of NaCl with three concentrations on the survival of *L. plantarum* KLDS 1.0328 were shown in Table 4, and the protective effects of multiple encapsulation matrix on strains, when microorganisms were exposed to 2%, 4% and 6% NaCl, were studied. When treated with 2% NaCl for 3 h, the count of viable cells of *L. plantarum* KLDS 1.0328 in PVOH/GA and MD/GA was not significantly reduced (P>0.05). When the NaCl concentration was 4%, the viable cell count of *L. plantarum* KLDS 1.0328 packaged in multiple materials was significantly higher than that of free *L. plantarum* KLDS 1.0328 (P<0.05). However, when the NaCl concentration was 6%, 11 g CFU/g was reduced in all the encapsulation materials. Compared with free *L. plantarum* KLDS 1.0328, the electrospun fibers or electrosprayed capsules of different materials can significantly enhance the tolerance of *L. plantarum* KLDS 1.0328 under osmotic stress (4% and 6% NaCl) treatment (P<0.05). High salt concentrations could disrupt the stability of the encapsulation matrix through ions, reducing protection while the encapsulation matrix ruptures, and probiotics were subsequently impaired by high concentrations of NaCl. Therefore, for foods with high salt content, MD/GA electrospraying encapsulation technology may not be the most effective way. However, in this study, *L. plantarum* KLDS 1.0328 could be protected against harsh osmotic media, even after the physical barrier formed by the biopolymer/GA complex was ruptured, possibly because these matrix formulations increased the stiffness of the bacterial cell wall and provided a local buffering effect.

Note: in the same column, different lowercase letters indicated that there were significant differences between the samples varying in composition (P<0.05); and in the same row, different capital letters indicated that there were significant differences between different osmotic stress treatments (P<0.05).

The survival rate of probiotics was often significantly affected by the heat treatment methods in the food industry, which in turn affected their probiotic function. Thus, the electrospinning or electrospraying encapsulation technologies that could be operated at ambient temperature were a promising way to improve probiotic tolerance. It can be seen from Table 5 that there was no significant difference among different encapsulated *L. plantarum* KLDS 1.0328 cells in terms of the viability cell count (P>0.05) after treated at 50° C. for 30 min; while the free *L. plantarum* KLDS 1.0328 cells suffered significant decline in the viability under the heat stress at 50° C. or above (P<0.05). In contrast, the cell viability of *L. plantarum* KLDS 1.0328 encapsulated in electrospun fibers and the electrosprayed capsules under the heat stress at 50° C. was similar to that of the control group without stress (P>0.05). When the temperature was further increased to 60° C., the viable cell count of free *L. plantarum* KLDS 1.0328 decreased by about 5.34 lg CFU/g, while the viability of the cells encapsulated in the electrospun fibers and the electrosprayed capsules only declined by 0.29~0.94 lg CFU/g. The heat stress at 60° C. or above will significantly weaken the viability of the encapsulated cells (P<0.05). The electrospun fibers and electrosprayed capsules varying in composition differed somewhat in the protective effect on *L. plantarum* KLDS 1.0328 during the whole exposure period to heat stress. By comparison, PVP/GA electrospun fiber and MD/GA electrosprayed capsule were more sensitive to the heat stress, and the viable cell count decreased by about 31 g CFU/g under the exposure to 70° C. for 30 min. The *L. plantarum* KLDS 1.0328 viable cell counts of all encapsulation groups were higher than 6 lg CFU/g. This result may be attributed to the synergistic effect between the biopolymer and the GA, which made the formed continuous network structure more closely intertwined, thereby forming a denser structured matrix around the probiotic, acting as a protective barrier to heat stress, and preventing the diffusion of heat and moisture into the electrospun fibers or electrosprayed capsules. As a consequence, the biopolymer-GA network can enhance the resis-

TABLE 4

Viability of free and encapsulated *L. plantarum* KLDS 1.0328 under different osmotic stress

| Samples | Viable cell count (lg CFU/g) | | | |
|---|---|---|---|---|
| | Control group | 2% NaCl | 4% NaCl | 6% NaCl |
| Free *L. plantarum* | 9.75 ± 0.04 $^{Aa}$ | 9.21 ± 0.06 $^{Ba}$ | 7.96 ± 0.08 $^{Cc}$ | 6.91 ± 0.15 $^{Dd}$ |
| PVOH/GA/*L. plantarum* | 9.38 ± 0.05 $^{Ab}$ | 9.18 ± 0.07 $^{ABa}$ | 9.03 ± 0.11 $^{Ba}$ | 8.55 ± 0.14 $^{Ca}$ |
| PVP/GA/*L. plantarum* | 9.26 ± 0.08 $^{Abc}$ | 9.04 ± 0.10 $^{Bab}$ | 8.57 ± 0.09 $^{Cb}$ | 8.06 ± 0.06 $^{Db}$ |
| WPC/GA/*L. plantarum* | 9.33 ± 0.11 $^{Abc}$ | 8.86 ± 0.09 $^{Bb}$ | 8.52 ± 0.07 $^{Cb}$ | 8.28 ± 0.07 $^{Dab}$ |
| MD/GA/*L. plantarum* | 9.15 ± 0.10 $^{Ac}$ | 8.94 ± 0.08 $^{Ab}$ | 8.43 ± 0.15 $^{Bb}$ | 7.45 ± 0.10 $^{Cc}$ |

NOTE:
in the same column, different lowercase letters indicated that there were significant differences between the samples varying in composition (P < 0.05); and in the same row, different capital letters indicated that there were significant differences between different osmotic stress treatments (P < 0.05).

tance of *L. plantarum* KLDS 1.0328 to the humidity and heat stress. The above results demonstrated that the obtained electrospun fibers or electrosprayed capsules can be used as a good carrier for encapsulating *L. plantarum* KLDS 1.0328 under humidity and heat stress conditions.

TABLE 5

Viability of free and encapsulated *L. plantarum* KLDS 1.0328 under different humidity and heat stress conditions

| Samples | Viable cell count (lg CFU/g) | | | |
|---|---|---|---|---|
| | Control group | 50° C. | 60° C. | 70° C. |
| Free *L. plantarum* | 9.75 ± 0.04 $^{Aa}$ | 8.90 ± 0.06 $^{Ba}$ | 4.41 ± 0.25 $^{Cc}$ | — |
| PVOH/GA/ *L. plantarum* | 9.38 ± 0.05 $^{Ab}$ | 9.18 ± 0.14 $^{Aa}$ | 9.09 ± 0.13 $^{Aa}$ | 6.79 ± 0.21 $^{Ba}$ |
| PVP/GA/*L. plantarum* | 9.33 ± 0.11 $^{Abc}$ | 9.04 ± 0.19 $^{Aa}$ | 8.32 ± 0.17 $^{Bb}$ | 6.23 ± 0.22 $^{Cb}$ |
| WPC/GA/*L. plantarum* | 9.26 ± 0.08 $^{Abc}$ | 9.12 ± 0.09 $^{ABa}$ | 8.95 ± 0.08 $^{Ba}$ | 6.89 ± 0.06 $^{Ca}$ |
| MD/GA/*L. plantarum* | 9.15 ± 0.10 $^{Ac}$ | 9.04 ± 0.15 $^{Aa}$ | 8.86 ± 0.16 $^{Aa}$ | 6.17 ± 0.14 $^{Bb}$ |

NOTE:
in the same column, different lowercase letters indicated that there were significant differences between the samples varying in composition (P < 0.05); and in the same row, different capital letters indicated that there were significant differences between different humidity and heat stress conditions (P < 0.05).

Note: in the same column, different lowercase letters indicated that there were significant differences between the samples varying in composition (P<0.05); and in the same row, different capital letters indicated that there were significant differences between different humidity and heat stress conditions (P<0.05).

3.7 Storage Stability Analysis of Free and Encapsulated *L. plantarum* KLDS 1.0328

Figure 9A:
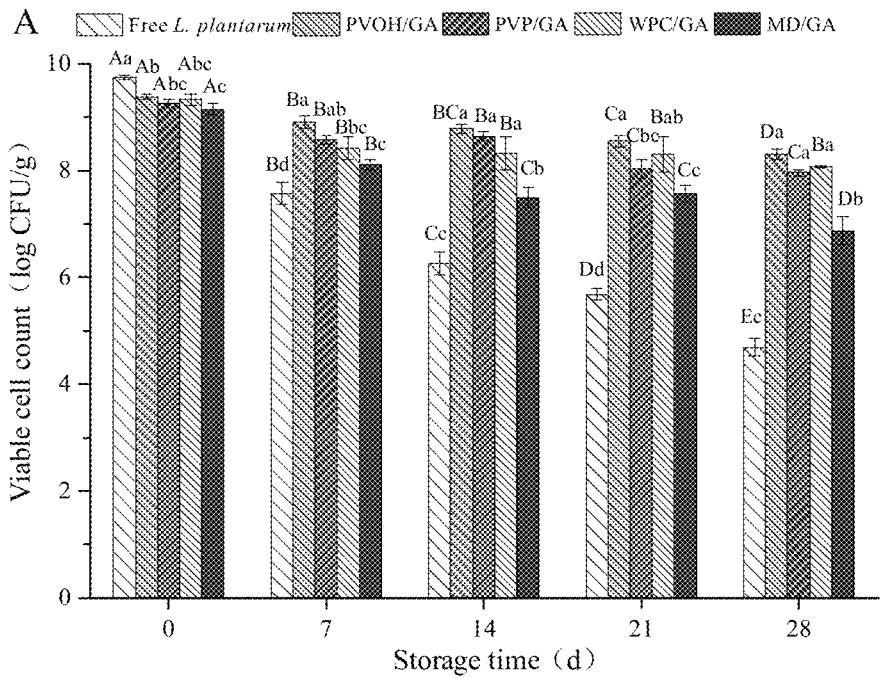
FIGS. 9A-9B shows viability of free *L. plantarum* KLDS 1.0328 and *L. plantarum* KLDS 1.0328 encapsulated in electrospun fibers/electrosprayed capsules during 28-day storage at 4° C. (9A) and 25° C. (9B) (notes: different lowercase letters indicate that there is significant difference between different samples at the same storage time in the viable cell count ($P<0.05$), and different capital letters indicate that for the same sample, there is significant difference in the viable cell count between different storage times ($P<0.05$))
Figure 9B:
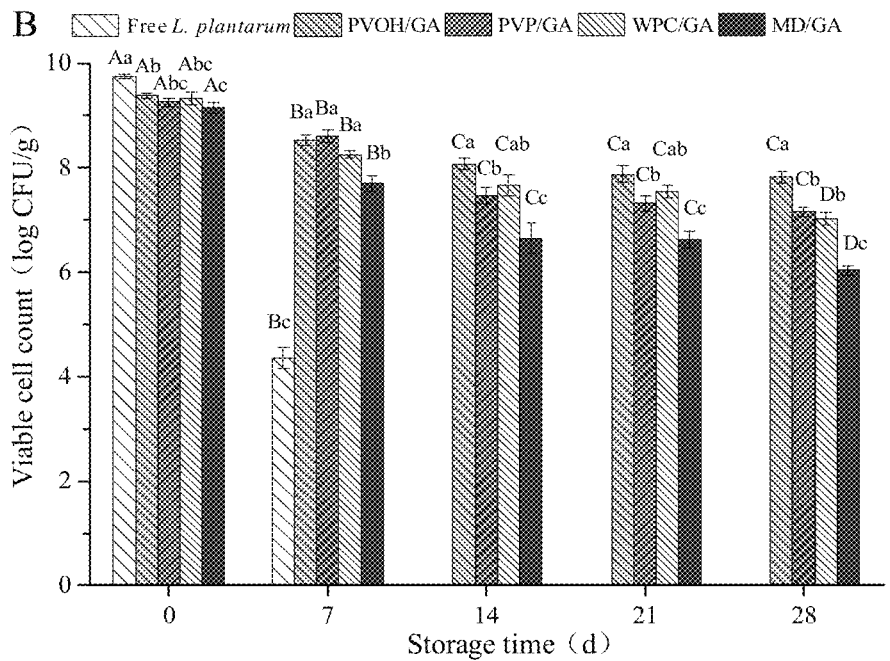

It was well known that in order to achieve the expected benefits for host health, it was necessary to ensure that there was an effective amount of probiotics surviving in the food at the time of consumption. Therefore, it was required to ensure the survival of encapsulated probiotics during the processing and storage stages. The viability of free *L. plantarum* KLDS 1.0328 and *L. plantarum* KLDS 1.0328 encapsulated in electrospun fibers/electrosprayed capsules during 28-day storage at 4° C. (FIG. 9A) and 25° C. is shown in FIGS. 9A and 9B, respectively. The results showed that the number of the surviving cells in encapsulated *L. plantarum* KLDS 1.0328 was significantly better than that of unencapsulated bacteria during storage at two temperatures. The number of free *L. plantarum* KLDS 1.0328 at 4° C. and 25° C. decreased significantly with the increase in storage time (P<0.05). Samples were kept at room temperature, and the activity of unpackaged *L. plantarum* KLDS 1.0328 was completely lost after 14 days. Thus, the commercially available foods containing probiotics must be stored at a temperature of 2~8° C. The storage stability test at 4° C. also confirmed that in addition to the relatively low storage stability of the MD/GA electrosprayed capsules, the viability of *L. plantarum* KLDS 1.0328 between the selected electrospun fibers or electrosprayed capsules had little difference during the storage for 28 days; and after 28 days, PVOH/GA, PVP/GA nanofibers and WPC/GA electrosprayed capsules still contained the large viable cell count (higher than 8 lg CFU/g).

Furthermore, compared to 25° C., the survival rate of *L. plantarum* KLDS 1.0328 in encapsulated samples stored at 4° C. was significantly higher, which may be due to the reduced metabolism of bacteria at low temperatures, which also indicated the effect of storage temperature on the survival and protection of encapsulated probiotics. In addition, it was found that the viability of *L. plantarum* KLDS 1.0328 after being encapsulated by different biopolymers was significantly reduced during storage at 25° C. for 28 days, and the survival rate depended on the composition of the electrospun fibers or electrosprayed capsules. At the end of 28 days of storage at 25° C., there was no significant difference in the viable cell count between PVP/GA and WPC/GA matrix (P>0.05); and compared with the PVP/GA and WPC/GA, PVOH/GA significantly enhanced the viability of *L. plantarum* KLDS 1.0328, and the viable cell count at the end of storage reached (7.88±0.16) lg CFU/g. Compared with other encapsulation materials, the inactivation rate of bacteria in MD/GA matrix was significantly higher (P<0.05), and the viable cell count at the end of storage was only (7.88±0.16) lg CFU/g. The above results showed that at the storage temperature of 4° C. or 25° C., a variety of the electrospun fibers and electrosprayed capsules used in this embodiment were all effective in protecting *L. plantarum* KLDS 1.0328, which could significantly enhance the stability of cells stored at 4° C. and 25° C. for 28 days.

3.8 Biological Characteristics of the Electrospun Fibers/Electrosprayed Capsules Encapsulated with *L. plantarum* KLDS 1.0328

Figure 10:
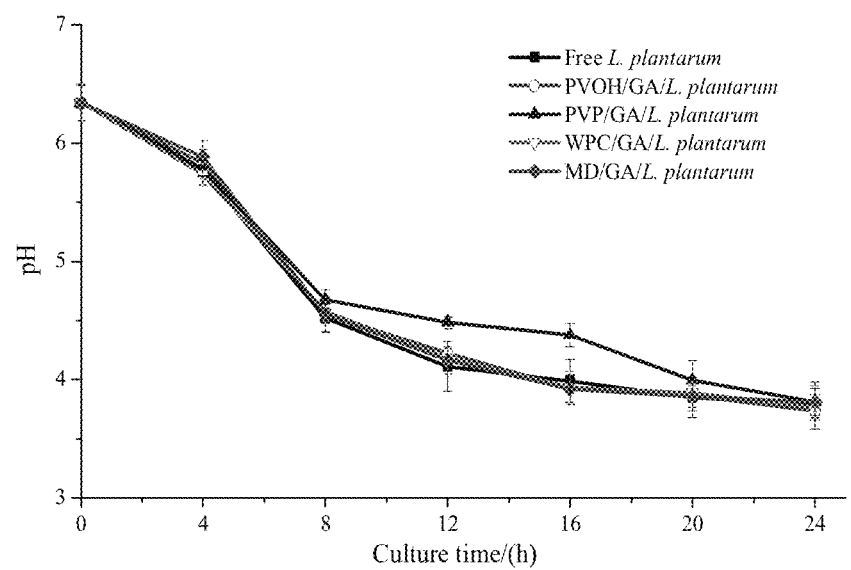
FIG. 10 shows change of pH of culture medium over time during the culture of free *L. plantarum* KLDS 1.0328 and *L. plantarum* KLDS 1.0328 encapsulated in electrospun fibers/electrosprayed capsules in MRS medium.

It was well known that during EHD process and subsequent storage, probiotics were subjected to environmental stresses such as high voltage electric field, shear force, osmotic stress, heat and oxidation, causing loss of cell viability. Therefore, it was necessary to investigate whether probiotics could maintain their properties and functions after encapsulation. The pH change of *L. plantarum* KLDS 1.0328 in MRS liquid medium after electrospinning and electrospraying processes was measured, and the results were shown in FIG. 10. The results showed that the acidification activity of *L. plantarum* KLDS 1.0328 in PVP/GA electrosprayed capsules in sterile MRS liquid medium was relatively slow compared with that of free *L. plantarum* KLDS 1.0328 during 12~16 h of culture, but at the end of fermentation, there was no significant difference in pH between *L. plantarum* KLDS 1.0328 encapsulated in PVP/GA electrosprayed capsules and free *L. plantarum* KLDS 1.0328 (P<0.05). In addition, there was no significant difference in the acidification kinetics process in MRS liquid medium between the free *L. plantarum* KLDS 1.0328 and the encapsulated *L. plantarum* KLDS 1.0328 (P<0.05).

Figure 11A:
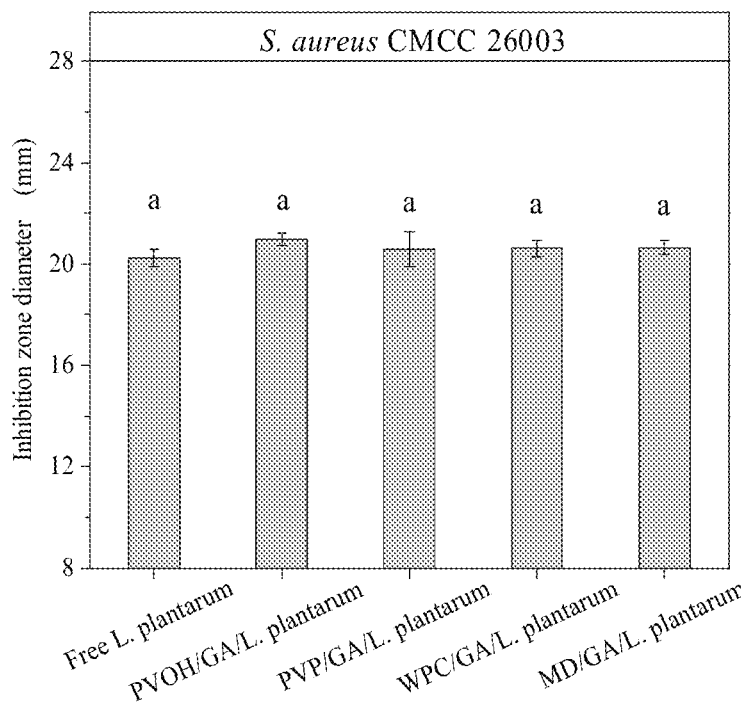
FIGS. 11A-11C shows inhibition effect of free *L. plantarum* KLDS 1.0328 and *L. plantarum* KLDS 1.0328 encapsulated in electrospun fibers/electrosprayed capsules on several kinds of pathogenic bacteria, where 11A: *Staphylococcus aureus* CMCC 26003; 11B: *Salmonella Typhimurium* ATCC 14028; and 11C: *Escherichia coli* ATCC 25922.
Figure 11B:
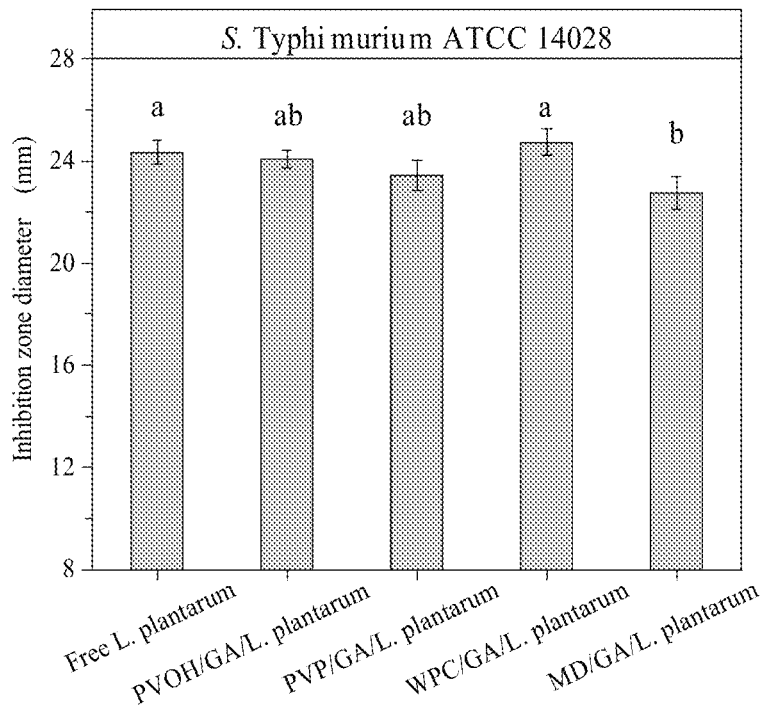
Figure 11C:
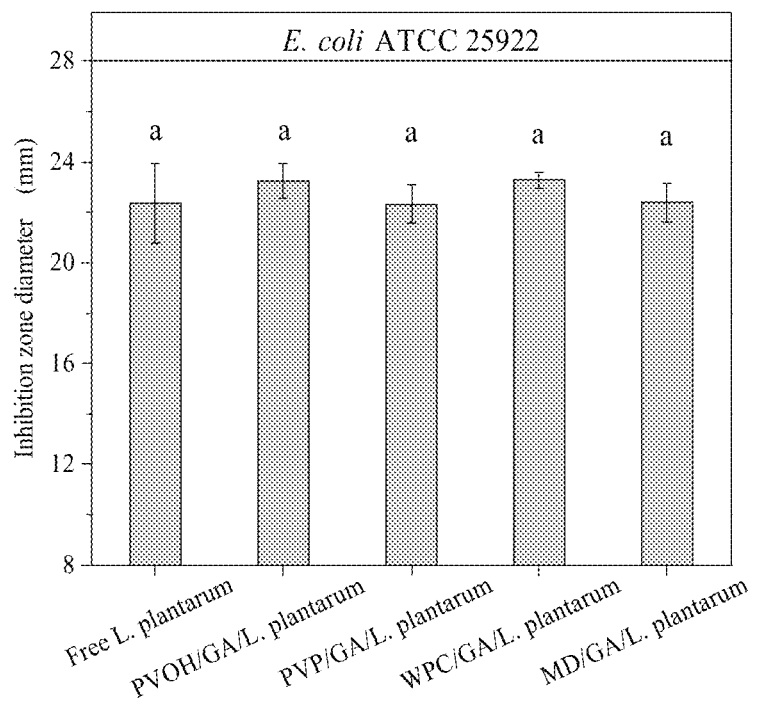

The inhibition effect of free *L. plantarum* KLDS 1.0328 and *L. plantarum* KLDS 1.0328 encapsulated in electrospun fibers/electrosprayed capsules on several kinds of pathogenic bacteria was shown in FIGS. 11A-11C (different lowercase letters indicate that there is significant difference in terms of viable cell count between different samples for the same pathogen (P<0.05)). It was found that *L. plantarum* KLDS 1.0328 still had the ability to inhibit *S. aureus* CMCC 26003, *S. Typhimurium* ATCC 14028 and *E. coli* ATCC 25922 after electrospinning and electrospraying treatment. Compared with free *L. plantarum* KLDS 1.0328 which were not encapsulated by the electrospun fibers or electrosprayed capsules, *L. plantarum* KLDS 1.0328 encapsulated in MD/GA electrosprayed capsules had significantly weaker antibacterial effect on *S. Typhimurium* ATCC 14028 (P<0.05), while there was no significant difference in the bacteriostatic activity for the same pathogen between other encapsulation test groups and free *L. plantarum* KLDS 1.0328 (P>0.05). The above test results showed that, overall, *L. plantarum* KLDS 1.0328 cells encapsulated in a variety of the electrospun fibers and electrosprayed capsules maintained their ability to inhibit pathogenic bacteria and had the potential to be probiotic products to inhibit or improve the infection of foodborne pathogens in the human intestine.

Thus, in the disclosure, the EHD technology combined with prebiotic constructed synergistically a homeostatic encapsulation system for *Lactobacillus*, thereby solving the problem of stable function of probiotics under environmental stress and providing a theoretical basis for further improving the effectiveness of probiotics in food applications.

*L. plantarum* KLDS 1.0328 was successfully encapsulated by the EHD technology in the electrospun fibers and the electrosprayed capsules which used the synthetic biopolymers such as PVOH and PVP, or food-grade polymer such as WPC and MD as the matrix and mixed with GA. After the introduction of GA or *L. plantarum* KLDS 1.0328, the conductivity and viscosity were increased. The conductivity of WPC/GA/*L. plantarum* KLDS 1.0328 solution was the highest, (28.17±0.31) mS/cm, and the viscosity of PVOH/GA/*L. plantarum* KLDS 1.0328 solution was (544.0±4.6) cp (P <0.05). It was observed from SEM images that the synthetic polymers PVOH/GA and PVP/GA encapsulated with *L. plantarum* KLDS 1.0328 formed the fibers with the local protrusions or beads or capsules, respectively, while natural polymers WPC/GA and MD/GA mainly formed capsules, with average diameters of (0.95±0.62) μm and (0.94±0.67) μm, respectively. Combined with the fluorescence microscope results, bacteria can be directionally wrapped along the nanofibers or randomly distributed in capsules. ATR FTIRs analysis revealed that there may be more intramolecular and intermolecular hydrogen bond interactions between the polymers and the bacteria. The thermal property analysis of the electrospun fibers and the electrosprayed capsules showed that the decomposition temperature of various encapsulation systems exceeded 300° C., which had the potential to be applied to heat treated food. The encapsulation rate of bacteria in PVOH/GA electrospun fibers was high, which was (96.50±1.14)%. Compared with free *L. plantarum* KLDS 1.0328, the survival rate of the *L. plantarum* KLDS 1.0328 in the above polymer/GA system was significantly improved after exposure to the simulated gastrointestinal stress. Specifically, the *L. plantarum* KLDS 1.0328 encapsulated in PVOH/GA matrix showed the highest survival rate (7.63±0.11) lg CFU/g, followed by WPC/GA capsules and PVP/GA fibers (>7.0 lg CFU/g); and the addition of the prebiotic GA significantly improved the ability of the electrosprayed capsules to resist simulated gastrointestinal stress (P<0.05). PVOH/GA electrospun fibers and WPC/GA electrosprayed capsules had strong resistance under osmotic stress and humid heat stress and had lower vitality loss after refrigeration at 25° C. and 4° C. for 28 days, but MD/GA showed lower stability for encapsulation. In addition, most of the *L. plantarum* KLDS 1.0328 still retained the primary metabolism, acid production and bacteriostatic ability after rehydration of the encapsulated matrix. In summary, the EHD technology has great potential in the encapsulation of probiotics and enhancement of the tolerance under environmental stress.

Described above are merely preferred embodiments of the disclosure, which are not intended to limit the disclosure. It should be understood that any modifications, replacements and improvements made by those skilled in the art without departing from the spirit of the disclosure should fall within the scope of the disclosure defined by the present claims.

What is claimed is:

1. A probiotic-encapsulating gum Arabic (GA) composite fiber/capsule, comprising:
   lactic acid bacteria; and
   an electrospun fiber or an electrosprayed capsule;
   wherein the lactic acid bacteria are encapsulated in the electrospun fiber or electrosprayed capsule; the electrospun fiber or electrosprayed capsule is prepared by compounding a biopolymer matrix with GA; the electrospun fiber or electrosprayed capsule consists of the biopolymer matrix, GA and polyoxyethylene (20) sorbitan monooleate; and the biopolymer matrix is selected from the group consisting of polyvinyl alcohol, polyvinylpyrrolidone and whey protein;
   when the biopolymer matrix is polyvinyl alcohol or polyvinylpyrrolidone, the probiotic-encapsulating GA composite fiber/capsule is prepared through steps of:
   (a1) preparing a suspension of the lactic acid bacteria; dissolving GA powder in water to obtain a GA solution; dissolving the polyvinyl alcohol or polyvinylpyrrolidone in water to obtain a biopolymer solution; and mixing the biopolymer solution with the GA solution uniformly to obtain a first mixed solution;
   (a2) adding the suspension of the lactic acid bacteria to the first mixed solution followed by uniform stirring to obtain a second mixed solution; and
   (a3) adding the polyoxyethylene (20) sorbitan monooleate to the second mixed solution followed by electrospinning to obtain the probiotic-encapsulating GA composite fiber or electrospraying to obtain the probiotic-encapsulating GA composite capsule;
   when the biopolymer matrix is the whey protein, the probiotic-encapsulating GA composite fiber/capsule is prepared through steps of:
   (b1) preparing a suspension of the lactic acid bacteria; dissolving GA powder in water to obtain a GA solution; adding the whey protein to the GA solution followed by mixing and stirring to obtain a first mixed solution;
   b2) adding the suspension of the lactic acid bacteria to the first mixed solution followed by uniform stirring to obtain a second mixed solution; and
   b3) adding the polyoxyethylene (20) sorbitan monooleate to the second mixed solution followed by electrospinning to obtain the probiotic-encapsulating GA composite fiber or electrospraying to obtain the probiotic-encapsulating GA composite capsule; and
   in step (a3), the polyoxyethylene (20) sorbitan monooleate is 5% of a weight of the polyvinyl alcohol or polyvinylpyrrolidone in the second mixed solution; and in step (b3), the polyoxyethylene (20) sorbitan monooleate is 5% of a weight of the whey protein in the second mixed solution.

2. The probiotic-encapsulating GA composite fiber/capsule of claim 1, wherein the lactic acid bacteria are *Lactobacillus plantarum* KLDS 1.0328.

3. The probiotic-encapsulating GA composite fiber/capsule of claim 1, wherein a diameter of the electrospun fiber is 150~170 nm, and a diameter of the electrosprayed capsule is 0.8~1.2 μm.

4. The probiotic-encapsulating GA composite fiber/capsule of claim 1, wherein in the steps (a1) and (b1), the suspension of the lactic acid bacteria is prepared through the following steps:
   inoculating the lactic acid bacteria into a deMan, Rosa and Sharpe (MRS) liquid medium at an inoculum amount of 2%, followed by anaerobic culture at 35~39° C. for 20~24 h and centrifugation at 4° C. and 5000×g for 10 min to collect cells; and washing the cells with a sterile phosphate-buffered saline (PBS) followed by resuspending with the PBS to a cell concentration of $10^9$~$10^{10}$ CFU/mL to produce the suspension of the lactic acid bacteria.

5. The probiotic-encapsulating GA composite fiber/capsule of claim 1, wherein in the step (a1), a weight/volume percent concentration of the GA solution is 20%; a weight/volume percent concentration of the biopolymer solution is 10%; and a weight ratio of the biopolymer solution to the GA solution is 8:2; and in the step (b1), a weight/volume percent concentration of the GA solution is 4%, and a weight/volume percent concentration of the whey protein in the first mixed solution is 20%.

6. The probiotic-encapsulating GA composite fiber/capsule of claim 1, wherein in the step (a2), a concentration of the lactic acid bacteria in the second mixed solution is $10^9$~$10^{10}$ CFU/mL; and in the step (b2), a concentration of the lactic acid bacteria in the second mixed solution is $10^9$~$10^{10}$ CFU/mL.

7. The probiotic-encapsulating GA composite fiber/capsule of claim 1, wherein in the steps (a3) and (b3), the electrospinning or the electrospraying is carried out at a voltage of 16~21 kV, a flow rate of 0.3~1.0 mL/h, and a distance of 10~16 cm.

* * * * *